United States Patent
Kennedy et al.

(10) Patent No.: US 11,284,615 B2
(45) Date of Patent: Mar. 29, 2022

(54) CRYOPRESERVATION USING SUCRALOSE

(71) Applicant: East Carolina University, Greenville, NC (US)

(72) Inventors: Anthony Kennedy, Greenville, NC (US); Jean-Luc Scemama, Greenville, NC (US); Jitka Virag, Greenville, NC (US); Edward R. Pennington, Albemarle, NC (US)

(73) Assignee: East Carolina University, Greenville, NC (US)

( * ) Notice: Subject to any disclaimer, the term of this patent is extended or adjusted under 35 U.S.C. 154(b) by 416 days.

(21) Appl. No.: 16/580,260

(22) Filed: Sep. 24, 2019

(65) Prior Publication Data

US 2020/0029552 A1 Jan. 30, 2020

Related U.S. Application Data

(62) Division of application No. 15/273,323, filed on Sep. 22, 2016, now Pat. No. 10,448,631.

(60) Provisional application No. 62/221,947, filed on Sep. 22, 2015.

(51) Int. Cl.
*A01N 1/02* (2006.01)
*A01N 3/00* (2006.01)
*C12N 5/04* (2006.01)
*C12N 5/07* (2010.01)
*C12N 5/078* (2010.01)

(52) U.S. Cl.
CPC ............. *A01N 1/0221* (2013.01); *A01N 3/00* (2013.01); *C12N 5/04* (2013.01); *C12N 5/0641* (2013.01)

(58) Field of Classification Search
None
See application file for complete search history.

(56) References Cited

U.S. PATENT DOCUMENTS

| | | | |
|---|---|---|---|
| 3,758,382 A | 1/1973 | Knorpp | |
| 4,473,552 A | 9/1984 | Jost | |
| 4,482,342 A | 11/1984 | Lueptow et al. | |
| 5,309,723 A | 5/1994 | Thomas et al. | |
| 5,384,311 A | 1/1995 | Antenucci et al. | |
| 5,480,773 A | 1/1996 | Ogata et al. | |
| 5,800,978 A | 9/1998 | Goodrich, Jr. et al. | |
| 5,958,670 A | 9/1999 | Goodrich, Jr. et al. | |
| 6,007,978 A | 12/1999 | Goodrich, Jr. et al. | |
| 6,673,607 B2 | 1/2004 | Toner et al. | |
| 6,773,877 B2 | 8/2004 | Fahy | |
| 7,270,946 B2 | 9/2007 | Brockbank et al. | |
| 2002/0009783 A1 | 1/2002 | Segall et al. | |
| 2005/0112269 A1 | 5/2005 | Ishibashi et al. | |
| 2005/0118129 A1 | 6/2005 | Xia et al. | |
| 2006/0188867 A1 | 8/2006 | Acker et al. | |
| 2006/0240163 A1 | 10/2006 | Catani et al. | |
| 2008/0299535 A1 | 12/2008 | Tokuda et al. | |
| 2014/0356948 A1 | 12/2014 | Jeon et al. | |
| 2015/0175955 A1 | 6/2015 | Comhaire et al. | |

FOREIGN PATENT DOCUMENTS

| | | |
|---|---|---|
| CA | 2128527 | 7/1993 |
| EP | 0 967 862 | 1/2003 |
| WO | WO 86/03938 | 7/1986 |
| WO | WO 92/08347 | 5/1992 |
| WO | WO 2013/117925 | 8/2013 |
| WO | WO 2015/191632 | 12/2015 |
| WO | WO 2015/191634 | 12/2015 |

OTHER PUBLICATIONS

U.S. Office Action corresponding to U.S. Appl. No. 16/413,121; dated Mar. 10, 2021 (13 pages).
Barker et al. "Using fluorescent probes to study the location and Interaction of disaccharides within lipid bilayers" *Poster Presented at the Southeastern Regional Meeting of the American Chemical Society* (1 page) (Nov. 4-7, 2015).
Barker et al. "Disruption of gel phase lipid packing efficiency by sucralose studied with merocyanine 540" *Colloids and Surfaces B: Biointerfaces* 152:214-219 (2017) (Abstract Only).
Biscardi et al. "Discrimination of the Hard Keratins Animal Horn and Chelonian Shell Using Attenuated Total Reflection-Infrared Spectroscopy" *Applied Spectroscopy* 66(5):606-608 (2012).
Bratosin et al. "Novel Fluorescence Assay Using Calcein-AM for the Determination of Human Erythrocyte Viability and Aging" *Cytometry Part A* 66A:78-84 (2005).
Cacela et al. "Low Amounts of Sucrose Are Sufficient to Depress the Phase Transition Temperature of Dry Phosphatidylcholine, but Not for Lyoprotection of Liposomes" *Biophysical Journal* 90:2831-2842 (2006).
Christensen et al. "Trehalose preserves DDA/TDB liposomes and their adjuvant effect during freeze-drying" *Biochimica et Biophysica Acta* 1768:2120-2129 (2007).
Coste et al. "Genetic integrity assessment of cryopreserved tomato (*Lycopersicon esculentum* Mill.) genotypes" *Turkish Journal of Biology* 39:638-648 (2015).
Crowe et al. "Anhydrobiosis" *Annual Review of Physiology* 54:579-599 (1992).
Crowe et al. "Stabilization of Membranes in Human Platelets Freeze-Dried With Trehalose" *Chemistry and Physics of Lipids* 122(1-2):41-52 (2003) (Abstract Only).
Deller et al. "Synthetic polymers enable non-vitreous cellular cryopreservation by reducing ice crystal growth during thawing" *Nature Communications* 5(3244):1-7 (2014).
Evans et al. "Ex Vivo Red Blood Cell Hemolysis Assay for the Evaluation of pH-responsive Endosomolytic Agents for Cytosolic Delivery of Biomacromolecular Drugs" *Journal of Visualized Experiments* (73):e50166 (2013).
Hasegawa et al. "Thermally Hydrated DPPC Langmuir Film: A Trial Application to the Analysis of Interaction of Sucrose with DPPC Liposome" *Journal of Physical Chemistry B* 101(3):6701-6706 (1997) (Abstract Only).

(Continued)

*Primary Examiner* — Michelle F. Paguio Frising
(74) *Attorney, Agent, or Firm* — Myers Bigel, P.A.

(57) ABSTRACT

Embodiments of the present invention relate to methods of preparing a cell, tissue, organ or plant for cryopreservation, wherein the method includes contacting the cell, tissue, organ or plant with a composition including sucrose and/or sucralose.

8 Claims, 22 Drawing Sheets

(56) References Cited

OTHER PUBLICATIONS

Hess, John R. "Conventional blood banking and blood component storage regulation: opportunities for improvement" *Blood Transfusion* 8(Suppl. 3):s9-s15 (2010).
Hmel et al. "Physical and thermal properties of blood storage bags: implications for shipping frozen components on dry ice" *Transfusion* 42(7):836-846 (2002) (Abstract Only).
Holovati et al. "Effects of Trehalose-Loaded Liposomes on Red Blood Cell Response to Freezing and Post-Thaw Membrane Quality" *Cryobiology* 58(1):75-83 (2009) (Abstract Only).
Kaschny et al. "The components of merocyanine-540 absorption spectra in aqueous, micellar and bilayer environments" *European Journal of Biochemistry* 207:1085-1091 (1992).
Kennedy et al. "Characterization of the Main Phase Transition in 1,2-Dipalomitoyl-Phosphatidylcholine Luvs by 1H NMR" *Journal of Liposome Research* (2002) (Abstract Only).
Kennedy et al. "The Interaction of DMSO with Model Membranes. II. Direct Evidence of DMSO Binding to Membranes: An NMR Study" *Journal of Liposome Research* 13(3-4):259-267 (2003).
Kennedy et al. "The association of dimethylsufoxide and model membranes studied by pulse-filed gradient NMR" *Journal of Spectroscopy* 18(2):265-269 (2004).
Kennedy et al. "Conservation of chemically degraded waterlogged wood with sugars" *Studies in Conservation* 59(3):194-201 (2014).
Konov et al. "Low-Temperature Molecular Motions in Lipid Bilayers in the Presence of Sugars: Insights into Cryoprotective Mechanisms" *The Journal of Physical Chemistry B* 118:12478-12485 (2014).
Long et al. "The Interaction of DMSO with Model Membranes. I. Comparison of DMSO and d$^s$-DMSO: A DSC and IR Investigation" *Journal of Liposome Research* 13(3 & 4):249-257 (2003).
Mazow et al. "Contamination in Organic Residue Analysis: A Cautionary Tale" *Journal of Eastern Mediterranean Archaeology and Heritage Studies* 2(2):90-109 (2014) (Abstract Only).
Oku et al. "A Simple Procedure for the Determination of the Trapped Volume of Liposomes" *Biochimica et Biophysica Acta-Biomembranes* 691(2):332-340 (1982) (Abstract Only).
Pallota et al. "Red blood cell processing for cryopreservation: from fresh blood to deglycerolization" *Blood Cells, Molecules and Diseases* 48(4):226-232 (2012) (Abstract Only).
Pennington et al. "Differential scanning calorimetry studies on the interactions between liposomes and sugars" Abstract submitted for the Southeastern Regional Meeting of the American Chemical Society (1 page) (Oct. 16-19, 2014) (available online Sep. 22, 2014).
Pennington et al. "Interactions of unilamellar DPPC bilayers with sucrose and sucralose: A DSC study" Poster Presented at the Southeastern Regional Meeting of the American Chemical Society (1 page) (Oct. 16-19, 2014).
Pennington et al. "Thermodynamics of interaction between carbohydrates and unilamellar dipalmitoyl phosphatidylcholine membranes" *Journal of Thermal Analysis and Calorimetry* 123:2611-2617 (2016).
Pennington et al. "Distinct membrane properties are differentially influenced by cardiolipin content and acyl chain composition in biomimetic membranes" *Biochimica et Biophysica Acta* 1859(2):257-267 (2017).
Rentas et al. "White particulate matter found in blood collection bags consist of platelets and leukocytes" *Transfusion* 7:959-966 (2004) (Abstract Only).
Repàkovà et al. "Distribution, Orientation, and Dynamics of DPH Probes in DPPC Bilayer" *The Journal of Physical Chemistry B* 108(35):13438-13448 (2004) (Abstract Only).
Russell et al. "Spectroscopic and Thermodynamic Evidence for Antimicrobial Peptide Membrane Selectivity" *Chemistry Physics of Lipids* 163:488-497 (2010) (Abstract Only).
Russell et al. "Determining the Effect of the Incorporation of Unnatural Amino Acids Into Antimicrobial Peptides on the Interactions with Zwitterionic and Anionic Membrane Model Systems" *Chemistry and Physics of Lipids* 164(8):740-758 (2011) (Abstract Only).
Schmid et al. "Red blood cell preservation by droplet freezing with polyvinyl pyrrolidone or sucrose/dextrose and by bulk freezing with glycerol" *Transfusion* 51(12):2703-2708 (2011).
Shimshick et al. "Lateral phase separation in phospholipid membranes" *Biochemistry* 12(12): 2351-2360 (1973) (Abstract Only).
Smith et al. "Using micropatterned lipid bilayer arrays to measure the effect of membrane composition on merocyanine 540 binding" *Biochimica et Biophysica Acta* 1808:1611-1617 (2011).
Sparrow, Rosemary L. "Time to revisit red blood cell additive solutions and storage conditions: a role for 'omics' analyses" *Blood Transfusion* 10(Suppl 2):s7-s11 (2012).
Sullivan et al. "Electrospinning and heat treatment of whey protein nanofibers" *Food Hydrocolloids* 35:36-50 (2014).
Tahira et al. "Mechanical Strength Studies on Degraded Waterlogged Wood Treated with Sugars" *Studies in Conservation* 62(4):223-228 (2016) (Abstract Only).
Thomas et al. "Electrochemical Anion Recognition by Novel Ferrocenyl Imidazole Systems" *Molecules* 7:861-866 (2002).
Virag et al. "Myofibroblast and Endothelial Cell Proliferation during Murine Myocardial Infarct Repair" *American Journal of Pathology* 163(6):2433-2440 (2003).
Virag et al. "Coronary Artery Ligation and Intramyocardial injection in a Murine Model of Infarction" *Journal of Visualized Experiments* 52(e2581):1-6 (2011).
Welsh et al. "Identification of Suspected Horn from the Queen Anne's Revenge (1718)" *The International Journal of Nautical Archaeology* 41:190-193 (2012).
Wong et al. "The Role of Physical Stabilization in Whole Blood Preservation" *Scientific Reports* 6(21023):1-9 (2016).
Yu et al. "Dimethyl Sulphoxide: A Review of Its Applications in Cell Biology" *Bioscience Reports* 14(6):259-281 (1994).
Zambelli et al. "Clinical Toxicity of Cryopreserved Circulating Progenitor Cells Infusion" *Anticancer Research* 18(6B):4705-4708 (1998) (Abstract Only).

(A) Sucrose  (B) Sucralose

Red blood cell count ~ 0.7 billion cells/ml, 3.5 x original

Red blood cell count ~ 1.4 billion cells/ml, 7 x original

Red blood cell count ~ 0.4 billion cells/ml, 2 x original

Red blood cell count ~ 0.7 billion cells/ml, 3.5 x original

Red blood cell count ~ 1.4 billion cells/ml, 7 x original

CRYOPRESERVATION USING SUCRALOSE

STATEMENT OF PRIORITY

This application is a divisional application of, and claims priority to, U.S. application Ser. No. 15/273,323, filed Sep. 22, 2016 (allowed), which claims the benefit of U.S. Provisional Patent Application Ser. No. 62/221,947, filed Sep. 22, 2015, the contents of each of which are incorporated by reference herein in their entirety.

RESERVATION OF COPYRIGHT

A portion of the disclosure of this patent document contains material which is subject to copyright protection. The copyright owner, East Carolina University, Greenville, N.C., a constituent institution of the University of North Carolina, has no objection to the reproduction by anyone of the patent document or the patent disclosure, as it appears in Patent Office patent files or records, but otherwise reserves all copyright rights whatsoever.

FIELD OF THE INVENTION

The present invention relates to methods and compositions useful for cryopreservation of cells, tissues, organs and plants.

BACKGROUND

Typically, freezing cells without adding some protective chemical will result in cell death. The cause of death is generally ice crystal formation, which punctures cells leading to cell death. The techniques for cryopreservation currently being used employ toxic chemicals winch must be removed from the cells before they are used or transfused. The toxicity of these chemicals, the cost and the need for specialized instrumentation has limited the use of cryopreservatives (CPs) in controlling damaging ice crystal formation within cells and cell membranes. Glycerol, a common CP used for storing frozen red blood cells (RBCs), must be removed using specialized equipment before transfusion of the cells into patients. Dimethylsulfoxide (DMSO), a common CP, has limited use due to adverse effects to many cell lines.

An understanding of the thermodynamics involved in the interactions between membranes and cryopreservatives may assist in advancing the field of cryopreservation.

As such, by replacing water in the membranes of cells, the likelihood of ice crystal formation is reduced, which in turn reduces the chance for cell death.

SUMMARY

Aspects of the present invention include methods of preparing a cell, tissue, organ or plant for cryopreservation, the method including contacting the cell, tissue, organ or plant with a composition including sucrose and/or sucralose.

Aspects of the present invention include methods for the cryopreservation of a cell, tissue or organ, including (a) contacting the cell, tissue, organ or plant with a composition including sucrose and/or sucralose; and (b) freezing the cell, tissue, organ, or plant.

Aspects of the present invention include methods of reducing ice crystal formation in a cell, tissue, organ or plant, the method including contacting the cell, tissue or organ with a composition including sucrose and/or sucralose, and subjecting the cell, tissue, organ or plant to a cryogenic temperature.

Aspects of the present invention include method of reducing cell death during cryopreservation, the method including contacting the cell, tissue, organ or plant with a composition including sucrose and/or sucralose and subjecting the cell, tissue, organ or plant to a cryogenic temperature.

Aspects of the present invention include methods of improved cryopreservation of a cell, tissue or organ compared to cryopreservation of a cell, tissue, organ or plant with glycerol or dimethylsulfoxide (DMSO), the method including contacting the cell, tissue, organ or plant with a composition including sucrose and/or sucralose.

Aspects of the present invention include a cryopreservation medium including sucrose and/or sucralose in a carrier suitable for cryopreservation.

Aspects of the present invention include a cryopreserved preparation of cells, tissues, organs or plants.

Aspects of the present invention include the use of sucrose and/or sucralose for the preparation of pharmaceutical compositions, transfusable preparations and transplantable preparations for the prevention or treatment of diseases and disorders for human and veterinary purposes and the pharmaceutical compositions, transfusable preparations and transplantable preparations.

Aspects of the present invention further include kits including one or more containers comprising cryopreserved cells as described herein or components to effectuate cryopreservation of cells, tissues, organs or plants.

DETAILED DESCRIPTION

Figure 1:
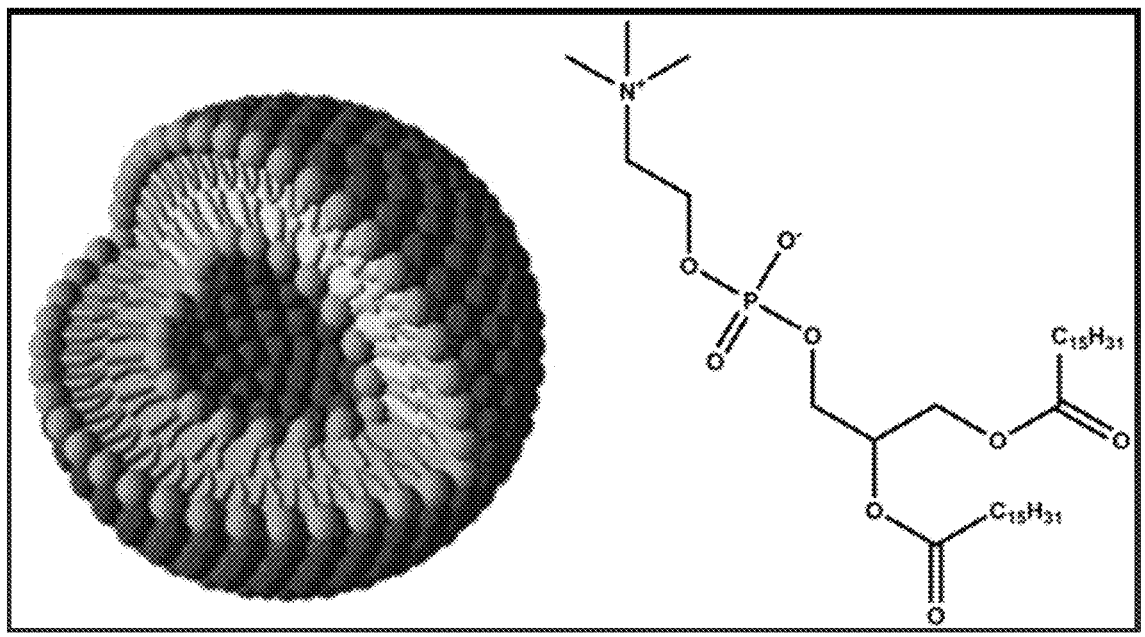
FIG. 1 shows the basic structure of a cell membrane.

This invention may be embodied in different forms and should not be construed as limited to the embodiments set forth herein. Rather, these embodiments are provided so that this disclosure will be thorough and complete, and will fully convey the scope of the invention to those skilled in the art.

The terminology used in the description herein is for the purpose of describing particular embodiments only and is not intended to be limiting of the invention. As used in the description and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description herein is for the purpose of describing particular embodiments only and is not intended to be limiting of the invention.

All patent and patent application references referred to in this patent application are hereby incorporated by reference in their entirety as if set forth fully herein.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the embodiments of the invention described herein may be used in any combination. For example, features described in relation to one embodiment may also be applicable to and combinable with other embodiments and aspects of the invention.

Moreover, the embodiments of the present invention also contemplate that in some embodiments, any feature or combination of features set forth herein may be excluded or omitted. To illustrate, if the specification states that a complex comprises components A, B and C, in some embodiments, any of A, B or C, or a combination thereof, may be omitted and disclaimed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

"Cryopreservation" or "cryoconservation" refers to a process whereby cells, tissues, organs or any other substances susceptible to damage caused by chemical reactivity or time can be preserved by cooling to sub-zero temperatures.

Cryogenic preservation of cells in suspension is a well-established and accepted technique for long term archival storage and recovery of live cells. As a general method, cells may be suspended in a cryopreservation media typically including salt solutions, buffers, nutrients, growth factors, proteins, and cryopreservatives. The cells are then distributed to archival storage containers of the desired size and volume, and the containers are then reduced in temperature until the container contents are frozen. Generally, long-term archival conditions may include liquid nitrogen gas storage where temperatures can be approximately −190° C.

The recovery of live cells and suitable tissues, organs and plants preserved by such methods is largely dependent upon minimizing injurious ice crystal growth in the intracellular region during both the freezing and thawing processes. A combination of two methods for reducing intracellular ice crystal growth is typically practiced in the freezing process. A cryoprotectant to permeate the cell membrane (or plant cell wall) and inhibit ice crystal nucleation and growth both extracellularly and intracellularly is desired as well as managing the reduction in sample temperature over time.

"Vitrification" refers to zero ice formation.

"Freezing" refers to a phase transition from which a liquid or semi-solid becomes a solid when its temperature is lowered to or below its freezing point.

"Crystallization" refers to the formation of a crystalline solid from or within a uniform liquid or semi-liquid resulting from the removal of heat.

"Subjects" as used herein are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, juvenile, adolescent, adult, and geriatric. Subjects may also include animal subjects, particularly mammalian subjects such as canines, felines, bovines, caprines, equines, ovines, porcines, rodents (e.g. rats and mice), lagomorphs, primates (including non-human primates), etc., for prevention and treatment purposes as well as veterinary medicine and/or pharmaceutical drug development purposes.

The term "cells" as used herein, refer to prokaryotic and eukaryotic cells. The cells used in accordance with the methods described herein may include primary cells that have been isolated from a tissue or organ, using one or more art-known proteases, e.g., collagenase, dispase, trypsin, or the like. The cells may be embryonic stem cells, embryonic germ cells, induced pluripotent stem cells, mesenchymal stem cells, bone marrow-derived mesenchymal stem cells (BM-MSCs), tissue plastic-adherent placental stem cells (PDACs), umbilical cord stem cells, amniotic fluid stem cells, amnion derived adherent cells (AMDACs), osteogenic placental adherent cells (OPACs), adipose stem cells, limbal stem cells, dental pulp stem cells, myoblasts, endothelial progenitor cells, neuronal stem cells, exfoliated teeth derived stem cells, hair follicle stem cells, dermal stem cells, parthenogenically derived stem cells, reprogrammed stem cells, amnion derived adherent cells, or side population stem cells. The cells used herein may also include blast cells, cloned cells, fertilized ova, placental cells, keratinocytes, basal epidermal cells, hair shaft cells, hair-root sheath cells, surface epithelial cells, basal epithelial cells, urinary epithelial cells, salivary gland cells, mucous cells, serous cells, von Ebner's gland cells, mammary gland cells, lacrimal gland cells, ceruminous gland cells, eccrine sweat gland cells, apocrine sweat gland cells, Moll gland cells, sebaceous gland cells, Bowman's gland cells, Brunner's gland cells, seminal vesicle cells, prostate gland cells, bulbourethral gland cells, Bartholin's gland cells, Littre gland cells, uterine endometrial cells, goblet cells of the respiratory or digestive tracts, mucous cells of the stomach, zymogenic cells of the gastric gland, oxyntic cells of the gastric gland, insulin-producing β cells, glucagon-producing α cells, somatostatin-producing Δ cells, pancreatic polypeptide-producing cells, pancreatic ductal cells, Paneth cells of the small intestine, type II pneumocytes of the lung, Clara cells of the lung, anterior pituitary cells, intermediate pituitary cells, posterior pituitary cells, hormone secreting cells of the gut or respiratory tract, thyroid gland cells, parathyroid gland cells, adrenal gland cells, gonad cells, juxtaglomerular cells of the kidney, macula densa cells of the kidney, peripolar cells of the kidney, mesangial cells of the kidney, brush border cells of the intestine, striated duct cells of exocrine glands, gall bladder epithelial cells, brush border cells of the proximal tubule of the kidney, distal tubule cells of the kidney, nonciliated cells of ductulus efferens, epididymal principal cells, epididymal basal cells, hepatacytes, fat cells, type I pneumocytes, pancreatic duct cells, nonstriated duct cells of the sweat gland, nonstriated duct cells of the salivary gland, nonstriated duct cells of the mammary gland, parietal cells of the kidney glomerulus, podocytes of the kidney glomerulus, cells of the thin segment of the loop of Henle, collecting duct cells, duct cells of the seminal vesicle, duct cells of the prostate gland, vascular endothelial cells, synovial cells, serosal cells, squamous cells lining the perilymphatic space of the ear, cells lining the endolymphatic space of the ear, choroids plexus cells, squamous cells of the pia-arachnoid, ciliary epithelial cells of the eye, corneal endothelial cells, ciliated cells having propulsive function, ameloblasts, planum semilunatum cells of the vestibular apparatus of the ear, interdental cells of the organ of Corti, fibroblasts, pericytes of blood capillaries, nucleus pulposus cells of the intervertebral disc, cementoblasts, cementocytes, odontoblasts, odontocytes, chondrocytes, osteoblasts, osteocytes, osteoprogenitor cells, hyalocytes of the vitreous body of the eye, stellate cells of the perilymphatic space of the ear, skeletal muscle cells, heart muscle cells, smooth muscle cells, myoepithelial cells, red blood cells, megakaryocytes, monocytes, connective tissue macrophages, Langerhan's cells, osteoclasts, dendritic cells, microglial cells, neutrophils, eosinophils, basophils, mast cells, plasma cells, helper T cells, suppressor T cells, killer T cells, immunoglobulin M, immunoglobulin G, immunoglobulin A, immunoglobulin E, killer cells, rod cells, cone cells, inner hair cells of the organ of Corti, outer hair cells of the organ of Corti, type I hair cells of the vestibular apparatus of the ear, type II cells of the vestibular apparatus of the ear, type II taste bud cells, olfactory neurons, basal cells of olfactory epithelium, type I carotid body cells, type II carotid body cells, Merkel cells, primary sensory neurons specialized for touch, primary sensory neurons specialized for temperature, primary neurons specialized for pain, proprioceptive primary sensory neurons, cholinergic neurons of the autonomic nervous system, adrenergic neurons of the autonomic nervous system, peptidergic neurons of the autonomic nervous system, inner pillar cells of the organ of Corti, outer pillar cells of the organ of Corti, inner phalangeal cells of the organ of Corti, outer phalangeal cells of the organ of Corti, border cells, Hensen cells, supporting cells of the vestibular apparatus, supporting cells of the taste bud, supporting cells of olfactory epithelium, Schwann cells, satellite cells, enteric glial cells, neurons of the central nervous system, astrocytes of the central nervous system, oligodendrocytes of the central nervous system, anterior lens epithelial cells, lens fiber cells, melanocytes, retinal pigmented epithelial cells, iris pigment epithelial cells, oogonium, oocytes, spermatocytes, spermatogonium, ovarian follicle cells, Sertoli cells, and thymus epithelial cells, or combinations thereof.

In some embodiments, the cells may be enucleated cells, for example, red blood cells. In other embodiments, the cells may be nucleated cells. In other embodiments, the cells may be plant cells. In yet other embodiments, the cells may comprise a tissue, a plant, or an organ, in whole or in part.

In some embodiments, cells may be cooled at a rate to a temperature between −30 and −80° C. or less. In some embodiments, cells may be frozen in liquid nitrogen, for example, at −196° C. In some embodiments, the cells may be stabilized at higher temperatures such as a room temperature (e.g., about 20-22° C.) and up to 30° C.

The term "tissue" as used herein, refers to a collection of single or multiple cell types. Non-limiting examples include connective tissue, muscle tissue (e.g., visceral (smooth) muscle tissue, skeletal muscle tissue, or cardiac muscle tissue), neural tissue generated in accordance with the methods described herein can comprise central nervous system tissue (e.g., brain tissue or spinal cord tissue) or peripheral nervous system tissue (e.g., cranial nerves and spinal nerves) and epithelial tissue (e.g., endothelium). "Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments, tissues may be cooled at a rate to a temperature between −30 and −80° C. or less. In some embodiments, tissues may be frozen in liquid nitrogen, for example, at −196° C. In some embodiments, the tissues may be stabilized at higher temperatures such as a room temperature (e.g., about 20-22° C.) and up to 30° C.

The term "organ" as used herein refers to a collection of tissues associated with any of the known mammalian organ systems, i.e., the digestive system, circulatory system, endocrine system, excretory system, immune system, integumentary system, muscular system, nervous system, reproductive system, respiratory system, and/or skeletal system. Exemplary organs that can be used in accordance with the methods described herein include, without limitation, lungs, liver, heart, brain, kidney, skin, bone, stomach, pancreas, bladder, gall bladder, small intestine, large intestine, prostate, testes, ovaries, spinal cord, pharynx, larynx, trachea, bronchi, diaphragm, ureter, urethra, esophagus, colon, thymus, and spleen.

In some embodiments, organs may be cooled at a rate to a temperature between −−30 and −80° C. or less. In some embodiments, organs may be subject to hypothermic temperatures. In some embodiments, tissues may be frozen in liquid nitrogen, for example, at −196° C. In some embodiments, the tissues may be stabilized at higher temperatures such as a room temperature (e.g., about 20-22° C.) and up to 30° C.

It is noted that a plant can include a "plant part" including, but not limited to, embryos, pollen, ovules, seeds, leaves, flowers, branches, fruit, stalks, roots, root tips, anthers, and/or plant cells including plant cells that are intact in plants and/or parts of plants, plant protoplasts, plant tissues, plant cell tissue cultures, plant calli, plant clumps, and the like.

Exemplary plants include, but are not limited to corn (*Zea mays*), canola (*Brassica napus, Brassica rapa* ssp.), alfalfa (*Medicago saliva*), rice (*Oryza sativa*, including without limitation Indica and/or Japonica varieties), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotiana tobacum*), potato (*Solanum, tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), duckweed (*Lemna*), oats (*Avena sativa*), barley (*Hordium vulgare*), vegetables, ornamentals, conifers, and turfgrasses (e.g., for ornamental, recreational or forage purposes), and biomass grasses (e.g., switchgrass and miscanthus).

Vegetables include *Solanaceous* species (e.g., tomatoes; *Lycopersicon esculentum*), lettuce (e.g., *Lactuea sativa*), carrots (*Caucus carota*), cauliflower (*Brassica oleracea*), celery (*Apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as Hubbard squash (*C. hubbard*), Butternut squash (*C. moschata*), Zucchini (*C. pepo*), Crookneck squash (*C. crookneck*), *C. argyrosperma, C. argyrosperma* ssp *sororia, C. digitata, C. ecuadorensis, C. foetidissima, C. lundelliana*, and *C. martinezii*, and members of the genus *Cucumis* such as cucumber (*Cucumis sativus*), cantaloupe (*C. cantalupensis*), and musk melon (*C. melo*).

Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherima*), and chrysanthemum.

Turfgrass include but are not limited to zoysiagrasses, bentgrasses, fescue grasses, bluegrasses, St. Augustinegrasses, bermudagrasses, bufallograsses, ryegrasses, and orchardgrasses.

Also included are plants that serve primarily as laboratory models, e.g. Arabidopsis.

"Reduce", "reducing," "reduction", and grammatical variants thereof, as used herein, refer to a decreased effect relative to what would occur in the absence of the methods of the present invention. In particular, such effects according to the present invention include a decrease in ice crystal formation and/or a decrease in cell death.

"Suitable carrier for cryopreservation" refers to a carrier that does not cause significant irritation to a cell, tissue or organ and does not abrogate the biological activity and/or properties of the administered compound thereby facilitating cryopreservation and/or successful thawing.

"Kit" as used herein refers to an assembly of components. The assembly of components can be a partial or complete assembly. Instructions for use of the kit or use of various components of the kit are optionally included.

Embodiments of the present invention provide methods and compositions useful for cryopreservation of cells, tissues and organs with such methods and compositions useful for the treatment of diseases and disorders in a subject in need thereof in addition to the cryopreservation of plants.

Compounds suitable for use according to the present invention include sucrose and sucralose. In some embodiments, the compound has the following structure for sucrose (A) or sucralose (B):

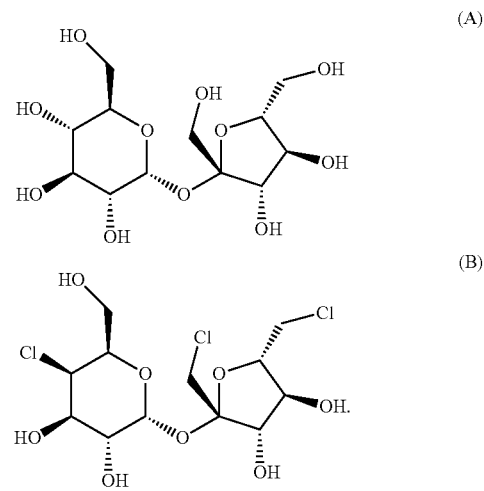

In some embodiments, the compound is 1,6-Dichloro-1, 6-dideoxy-β-D-fructofuranosyl-4-chloro-4-deoxy-α-D-galactopyranoside; (2R,3R,4R,5R,6R)-2-[(2R,3S,4S,5S)-2,5-Bis(chloromethyl)-3,4-dihydroxyoxolan-2-yl]oxy-5-chloro-6-(hydroxymethyl)oxane-3,4-diol; 1',4,6'-trichlorogalactosucrose; trichlorosucrose; E955; 4,1',6'-Trichloro-4,1',6'-trideoxygalactosucrose or TGS.

In some embodiments the sucrose and/or sucralose is present in a concentration in range from about 0.01% w/v to 30% w/v, 0.01% w/v to 20% w/v, 0.01% w/v to 10% w/v, 0.01% w/v to 1% w/v, 0.1% w/v to 1% w/v, 0.1% w/v to 1.5% w/v, 0.1% w/v to 2% w/v, or 0.1% w/v to 2.5% w/v, and including any numerical values included within the specified range limits. For example, sucrose and/or sucralose concentrations may be 0.125% w/v, 0.250% w/v, 0.375% w/v, 0.500% w/v, 0.625% w/v, 1.000% w/v, 1.250% w/v, 1.500% w/v, 1.750% w/v, 2.000% w/v, 2.25% w/v, or 2.500% w/v.

In particular embodiments, sucrose may be used alone, sucralose may be used alone or sucrose and sucralose may be used in combination in various ratios as determined by one of ordinary skill in the art to obtain the desired result.

In some embodiments, sucrose and/or sucralose may dehydrate the cell membrane thereby reducing or eliminating ice crystal formation and/or growth.

Embodiments of the present invention include methods of preparing a cell, tissue, organ or plant for cryopreservation, the method comprising, consisting essentially of, or consisting of contacting the cell, tissue, organ or plant with a composition comprising, consisting essentially of, consisting of sucrose and/or sucralose. Cells, tissues, organs and plants used in accordance with this invention are described above. In some embodiments, the cells are red blood cells.

In some embodiments, the present invention provides methods for the cryopreservation of a cell, tissue, plant or organ, comprising, consisting essentially of, or consisting of (a) contacting the cell, tissue, plant or organ with a composition comprising, consisting essentially of, or consisting of sucrose and/or sucralose; and (b) freezing the cell, tissue or organ. In some embodiments, the cell, tissue, organ or plant are contacted with the composition comprising, consisting essentially of, or consisting of sucrose and/or sucralose before the freezing step, during the freezing step, and/or after the freezing step.

Embodiments of the present invention also provide methods of reducing ice crystal formation in a cell, tissue, organ or plant, the method comprising, consisting essentially of, or consisting of contacting the cell, tissue, organ or plant with a composition comprising, consisting essentially of, or consisting of sucrose and/or sucralose and subjecting the cell, tissue, organ or plant to a cryogenic temperature. In some embodiments, the methods provide vitrification. In addition to reducing ice crystal formation, the methods provide greater success rates of obtaining suitable thawed cells, tissues, organs or plant for use after cryopreservation, i.e., improved recovery upon thawing.

In accordance with the present invention, further embodiments provide methods of reducing cell death during cryopreservation, the method comprising, consisting essentially of, or consisting of contacting the cell, tissue, organ or plant with a composition comprising, consisting essentially of, or consisting of sucrose and/or sucralose and subjecting the cell, tissue, organ or plant to a cryogenic temperature. In some embodiments, the cell, tissue, organ or plant are contacted with the composition comprising, consisting essentially of, or consisting of sucrose and/or sucralose before, during and/or being subjected to the cryogenic temperature. Thus, in addition to reducing cell death during cryopreservation, the methods provide greater success rates of obtaining suitable thawed cells, tissues, organs or plants for use after cryopreservation, i.e., improved recovery upon thawing.

In some embodiments of the present invention, methods of improved cryopreservation of a cell, tissue or organ compared to cryopreservation of a cell, tissue, organ or plant with glycerol or dimethylsulfoxide (DMSO), the method comprising, consisting essentially of, consists of contacting the cell, tissue, organ or plant with a composition comprising, consisting essentially of, consisting of sucrose and/or sucralose are provided.

Embodiments of the present invention further provide a cryopreservation medium comprising, consisting essentially of, or consisting of sucrose and/or sucralose in a carrier suitable for cryopreservation.

Embodiments of the present invention also provide cryopreserved preparations of cells, tissues or organs prepared by the methods recited herein.

In particular embodiments, the present invention provides compositions such as pharmaceutical compositions comprising, consisting essentially of, or consisting of the cells subjected to the methods described herein; transfusable preparations comprising, consisting essentially of, or consisting of the cryopreserved cells described herein; transplantable preparations comprising, consisting essentially of, or consisting of the tissues or organs subjected to the methods described herein.

Embodiments of the present invention further provide kits comprising, consisting essentially of, consisting of one or more containers comprising, consisting essentially of, or consisting of the cells subjected to the methods described herein and/or components for the cryopreservation of cells, tissues, organs and/or plants.

Some embodiments of the present invention are directed to use in subjects such as those described above. Additionally, subjects further include, but are not limited to, those in need of a cell transfusion and/or tissue and/or organ transplant.

When administered or used in a pharmaceutical manner, the cryopreserved cells, tissues or organs may be thawed and suitable for the intended use. They may be combined with a physiologically acceptable carrier. In some embodiments, the physiologically acceptable carrier can include, but is not limited to, sterile water, saline, glucose, dextrose, stabilizers (e.g., sugars and amino acids), preservatives, wetting agents, emulsifying agents, and pH buffering agents. Suitable carriers for pharmaceutical compositions are described in "Remington's Pharmaceutical Sciences" by E. W. Martin.

Suitable ranges of temperatures for the methods recited herein are discussed above. Cooling rates are generally fast, for example, up to 100° C./min. In terms of storage, once stabilized, storage time is generally directly related to the sugar stability/shelf life.

FIG. 1 shows the basic structure of a cell membrane and the type of molecule found within that membrane.

Figure 2:
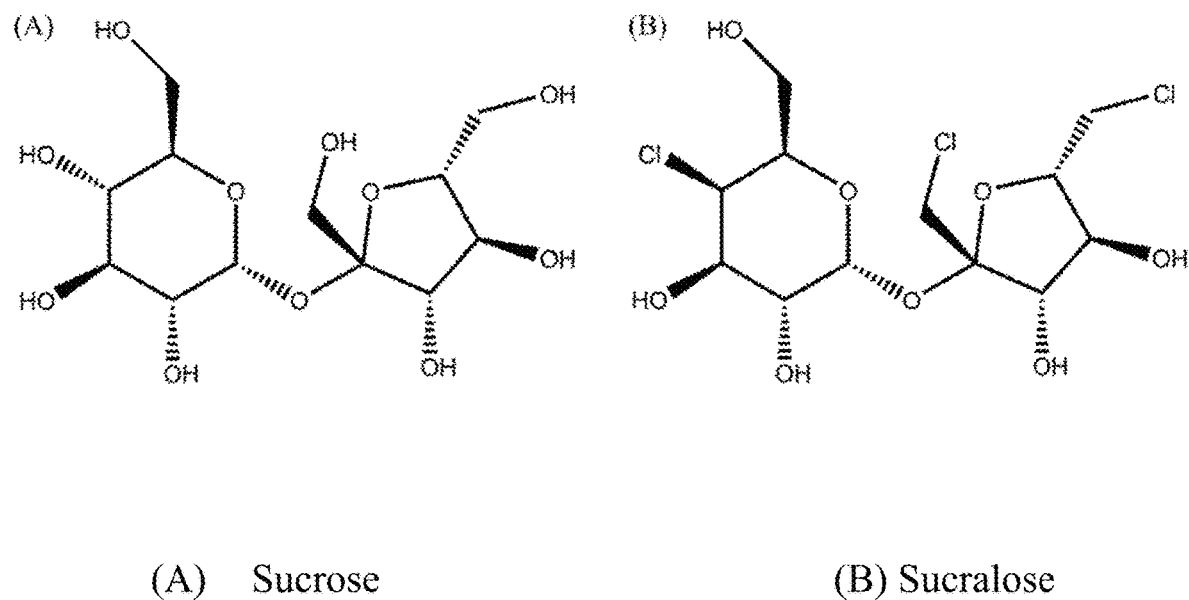
FIG. 2 shows the chemical structure of sucrose (table sugar) and sucralose.

FIG. 2 depicts the chemical structures of sucrose (table sugar) and sucralose.

Figure 3:
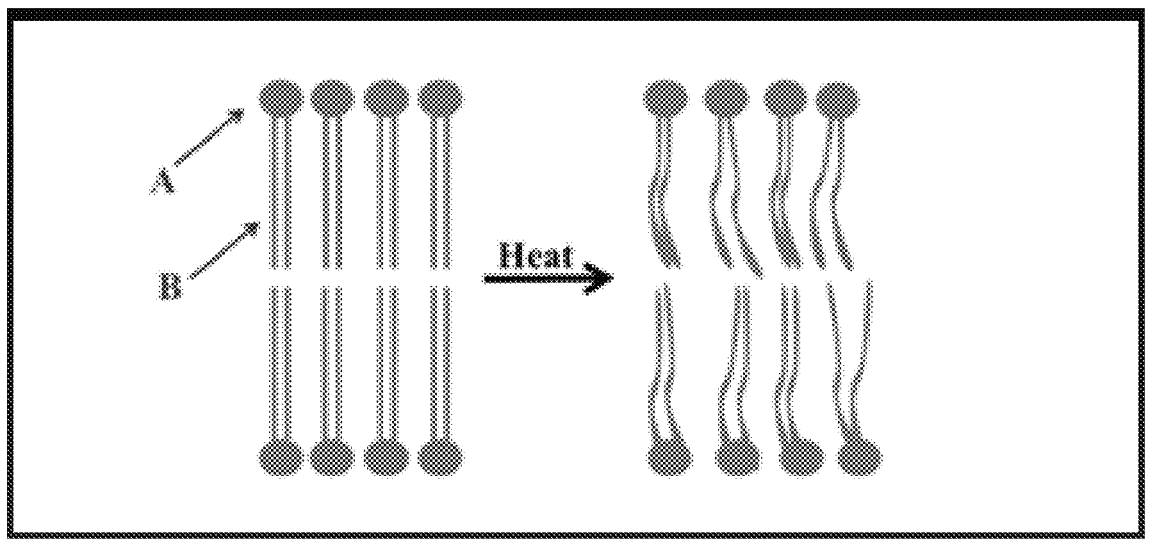
FIG. 3 shows a cartoon representation of a part of a cell membrane.

FIG. 3 shows a cartoon of how a cell membrane can "melt" when heat is applied. The polar head group is labeled A and the fatty acid chains are labeled B. Changes in the melting temperature can be monitored and used to interpret the effects of additives.

Figure 4:
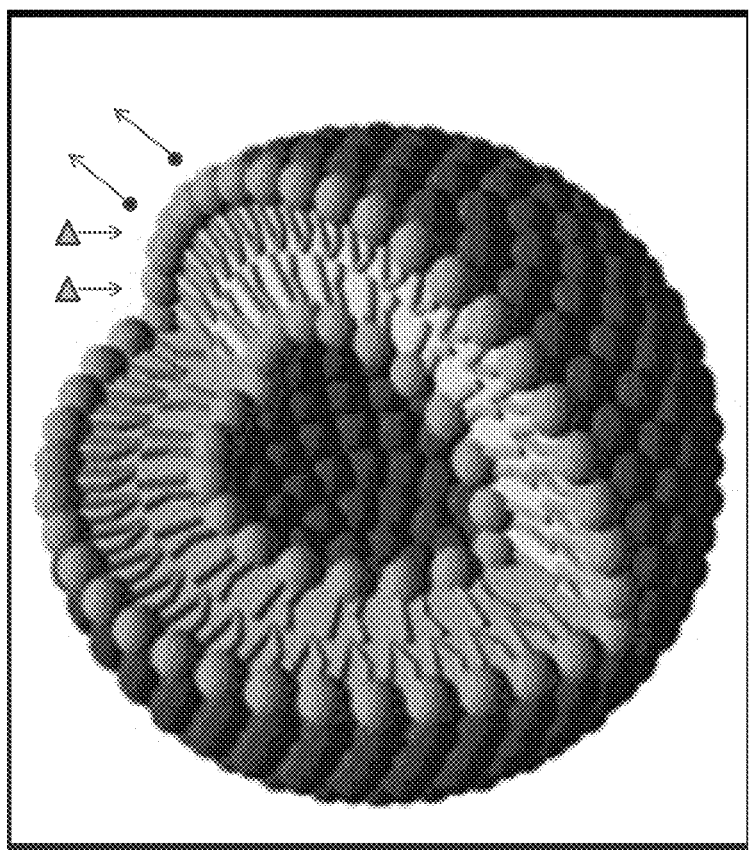
FIG. 4 shows the structure of a cell membrane, the water-sugar molecule relationship and how crystal formation is inhibited.

FIG. 4 shows how sugar/sucralose molecules replace water in the cell membrane, as a result, the thickness of the membrane decreases and ice crystal formation is inhibited.

Having described the present invention, the same will be explained in greater detail in the following examples, which are included herein for illustration purposes only, and which are not intended to be limiting to the invention.

EXAMPLES

Example 1

Interactions of Unilamellar DPPC Bilayers with Sucrose and Sucralose

Methods: Unilamellar vesicles were prepared by extrusion. Sucrose or sucralose was added to the vesicles to achieve the desired mole ratio after vesicle formation. Differential scanning calorimetry was used to examine the main phase behavior of the liposome bilayer. Thermograms were obtained in the heating and cooling directions between 30° C. and 60° C. at a rate of 2° C./min.

Figure 5:
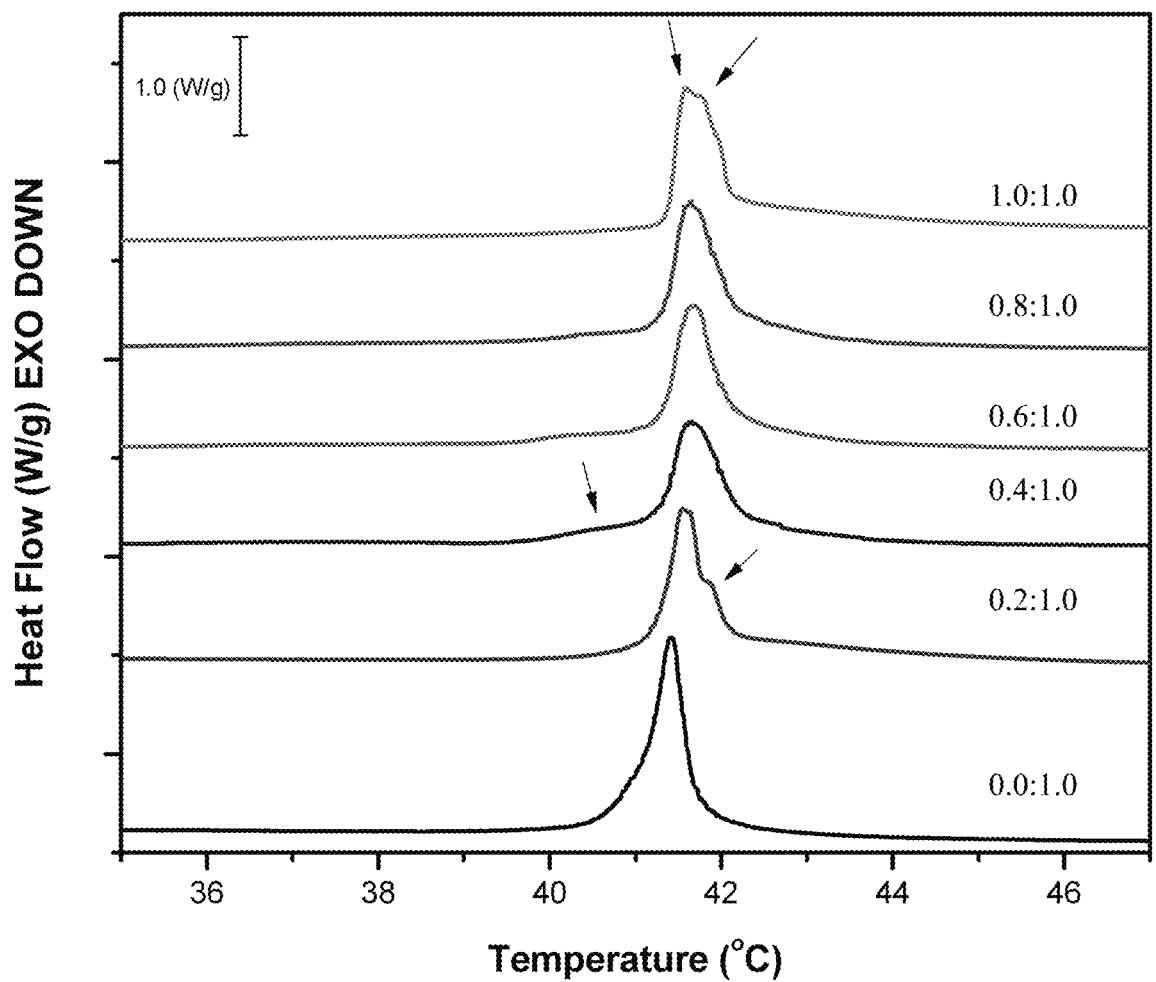
FIG. 5 shows thermograms of DPPC (heating cycle) in the presence of increasing amounts of sucrose. The mole ratios of sucrose to lipid examined are as indicated.
Figure 6:
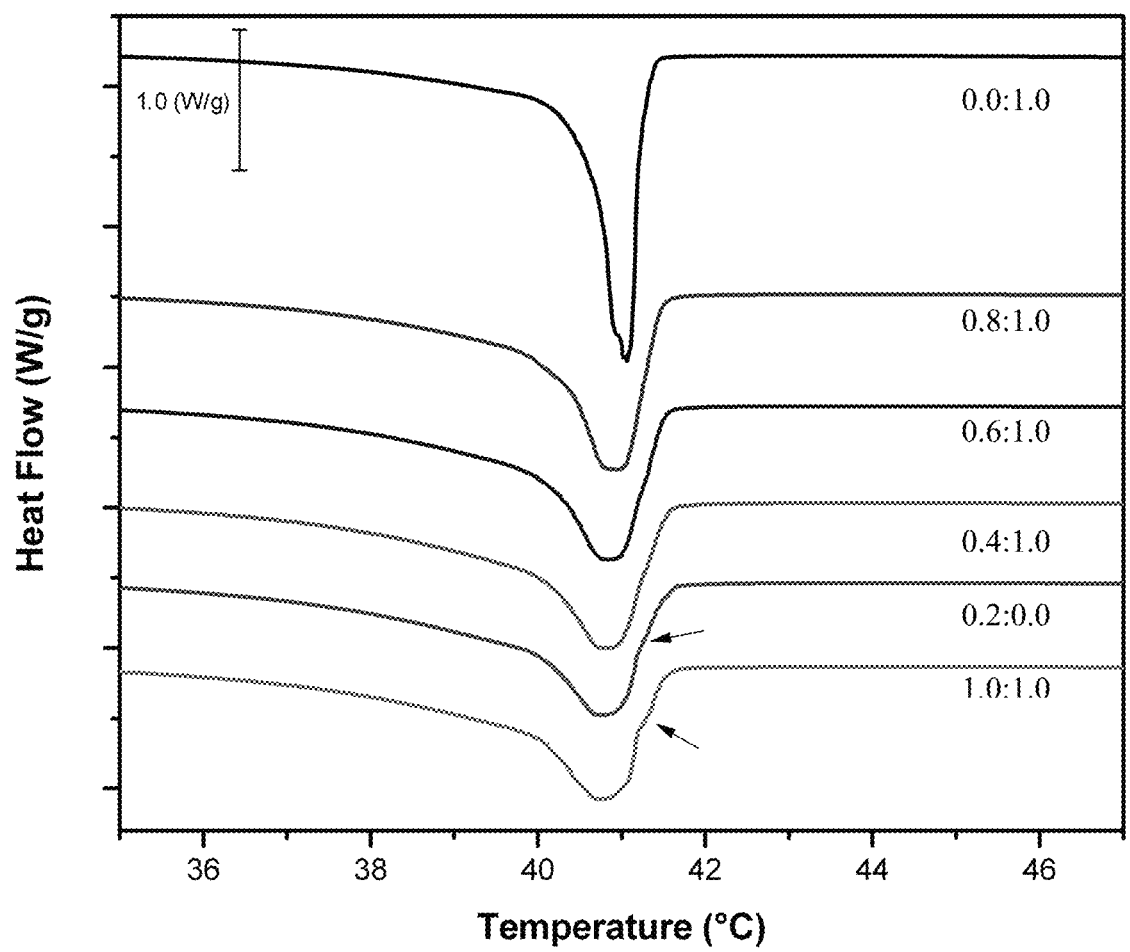
FIG. 6 shows thermograms of DPPC (cooling) in the presence of increasing amounts of sucrose. The mole ratios of sucrose to lipid examined are as indicated.

The main phase transition is observed at ~42° C. for dipalmitoyl phosphatidylcholine (DPPC) liposomes and exhibits little change upon addition of increasing amounts of sucrose. This is shown by the thermograms in FIG. 5 for heating, and in FIG. 6 for cooling.

Figure 7:
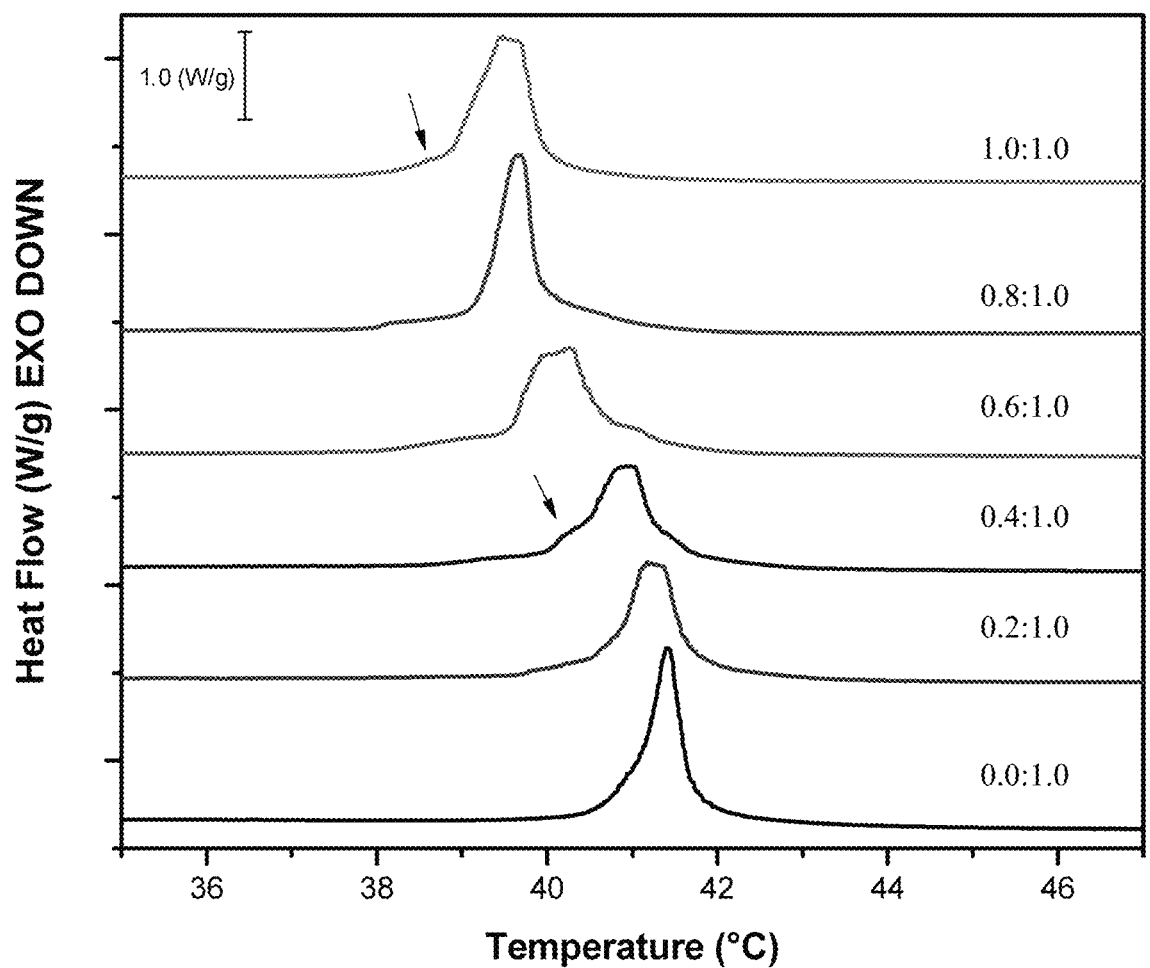
FIG. 7 shows thermograms of DPPC (heating cycle) in the presence of increasing amounts of sucralose. The mole ratios of sucralose to lipid examined are as indicated.
Figure 8:
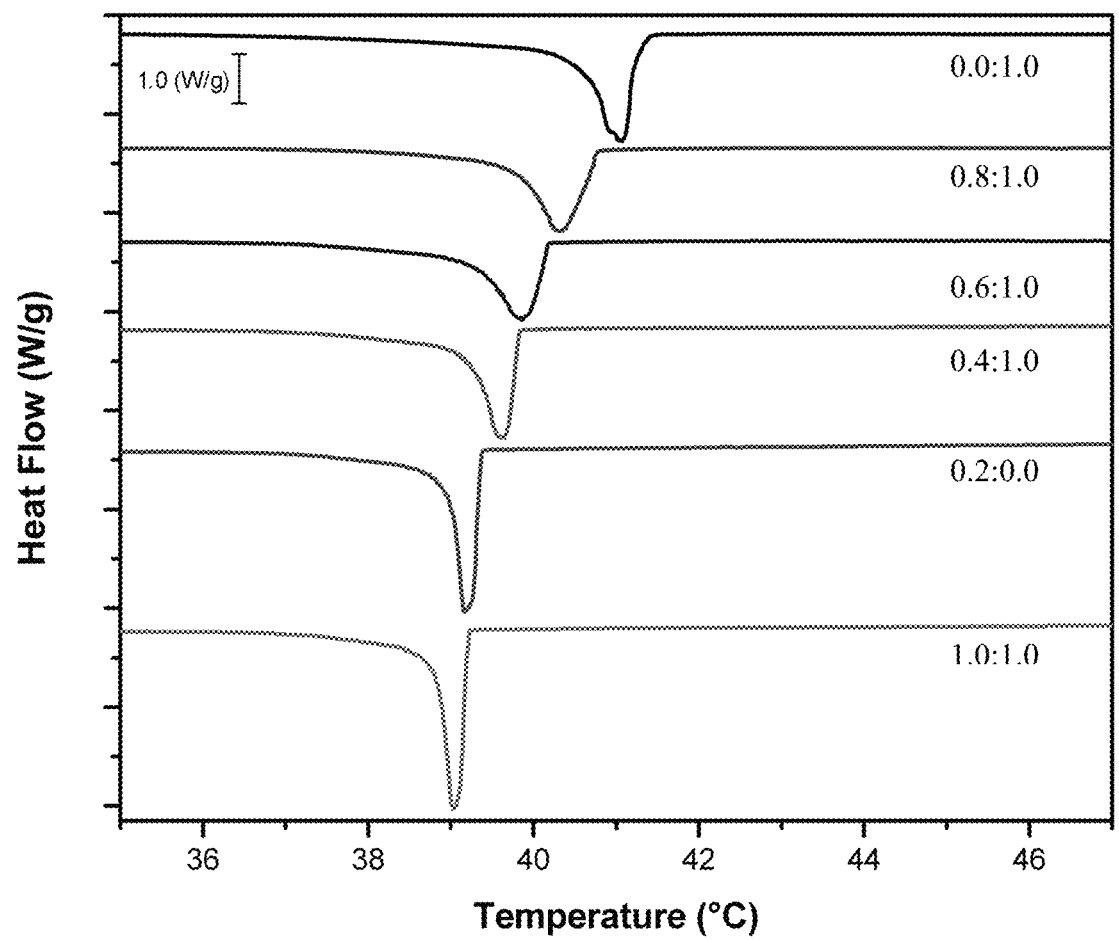
FIG. 8 shows thermograms of DPPC (cooling) in the presence of increasing amounts of sucralose. The mole ratios of sucralose to lipid examined are as indicated.

In addition to minimal changes in the main phase transition temperature the enthalpy remains relatively stable also, although large changes are seen in the peak width at half peak height (PWHH) which can be used as a rough qualitative estimate of the cooperativity of the transition. As sugar concentration increases so does the PWHH indicating a decrease in cooperativity. It was observed that shoulders appear (indicated with arrows) when sucrose is added which may be indicative of phase separation (Shimshick, E. J.; McConnell, H. M. Biochemistry (N.Y.) 1973, 12, 2351-2360). However, upon the addition of sucralose the phase behavior of DPPC liposomes was significantly altered. The main phase transition temperature for DPPC liposomes decreased significantly. This is shown by the thermograms in FIG. 7 for heating, and in FIG. 8 for cooling.

The observed decrease in the transition temperature could be due to destabilization of the gel phase upon incorporation of sucralose into the membrane, which would also explain the observed drastic decrease in cooperativity. The enthalpy however remained essentially unchanged. As in the case of sucrose a shoulder is seen in some thermograms which may be again associated with phase separation. Similar behavior was seen for both sugars during the corresponding cooling cycles. In the presence of sucrose shoulders are again observed but these are not seen for sucralose.

Figure 9:
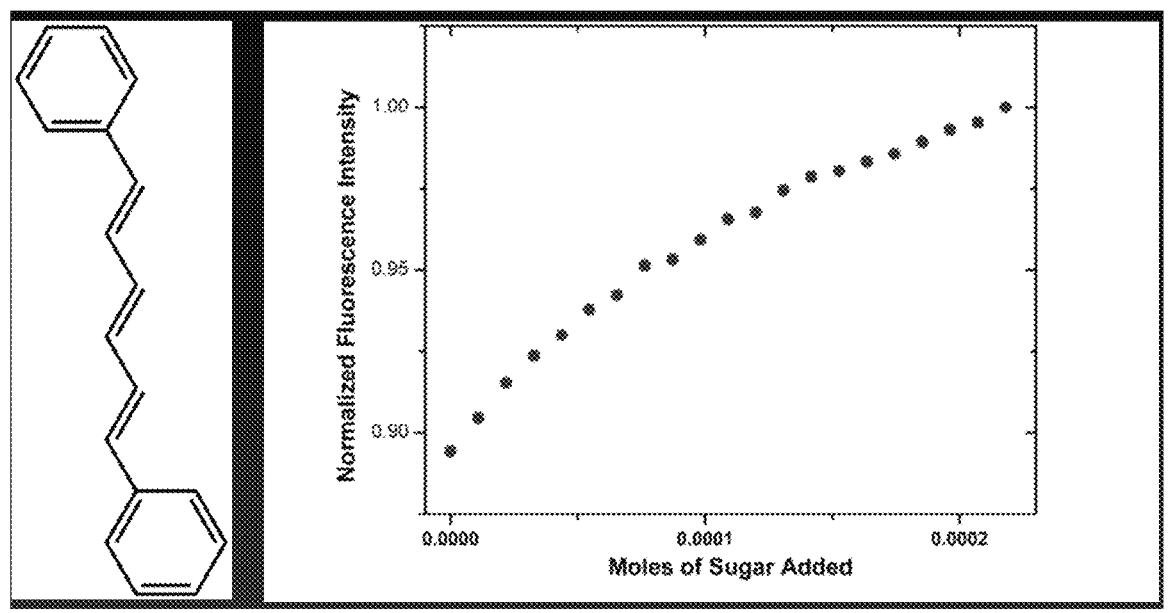
FIG. 9 shows the relation between fluorescence intensity of diphenylhexatriene (DPH) and increasing amounts of sucralose added.

A molecule used to examine changes in the membrane and a graph of the light produced by that molecule. In particular, the fluorescence intensity of diphenylhexatriene (DPH) increases as sucralose is added to model membranes, as shown in FIG. 9. DPH fluorescence is quenched by water so an observed increase upon addition of sugar indicates water is being removed from the vicinity of the membrane.

Experiments with merocyanine 540, a fluorescent probe sensitive to lipid packing, showed an increase in fluidity and a decrease in polarity of model membranes in the presence of increasing amounts of sucralose, both indicative of the displacement of water in membranes.

Example 2

Cryopreservation of Red Blood Cells

Experiments that measure the percent hemolysis of red blood cells before and after treatment were carried out using sheep blood.

This is data from blood frozen for 48 hours. The blood was not ideal as it was left in a warehouse overnight and arrived hot so the cells were very fragile, hence the relatively high hemolysis compared to previous data.

Figure 10:
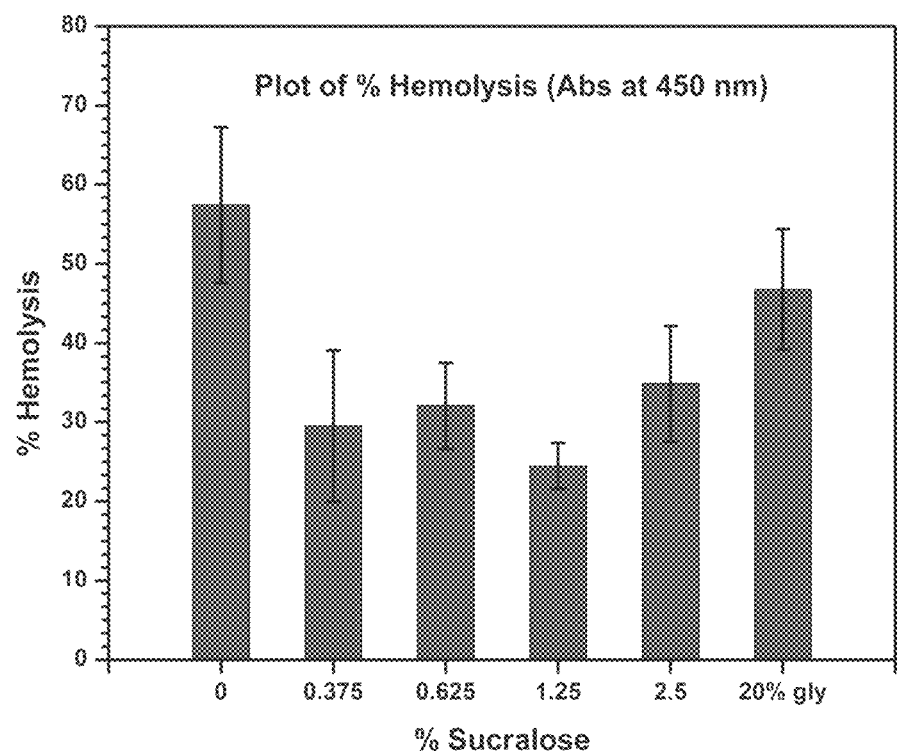
FIGS. 10, 11 and 12 show % hemolysis of red blood cells determined by absorption at 450 nm, 500 nm and 525 nm, respectively, in the presence of increasing amounts of sucralose.
Figure 11:
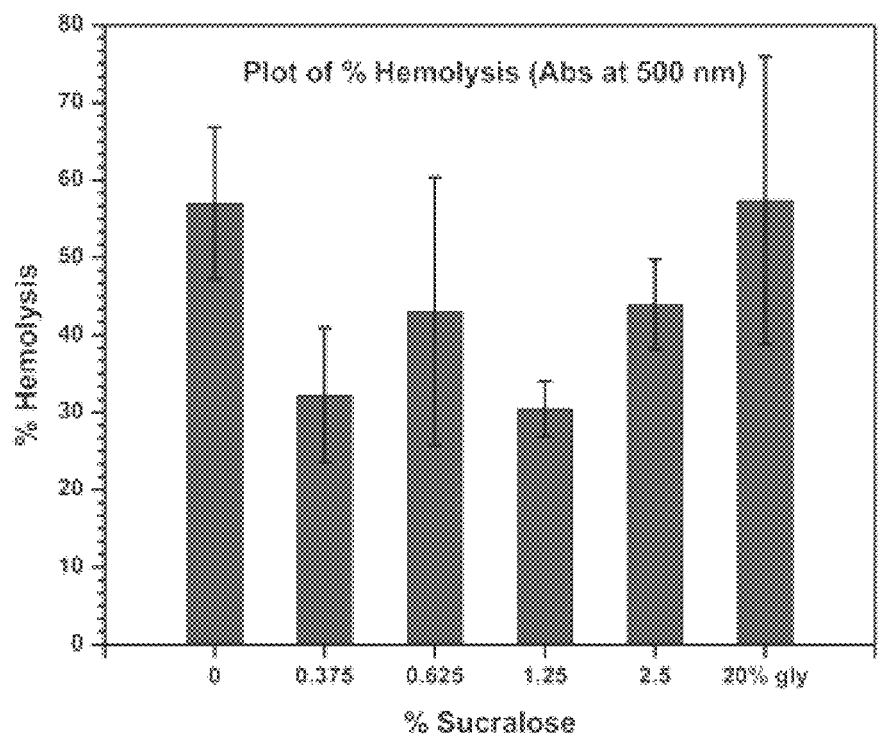
Figure 12:
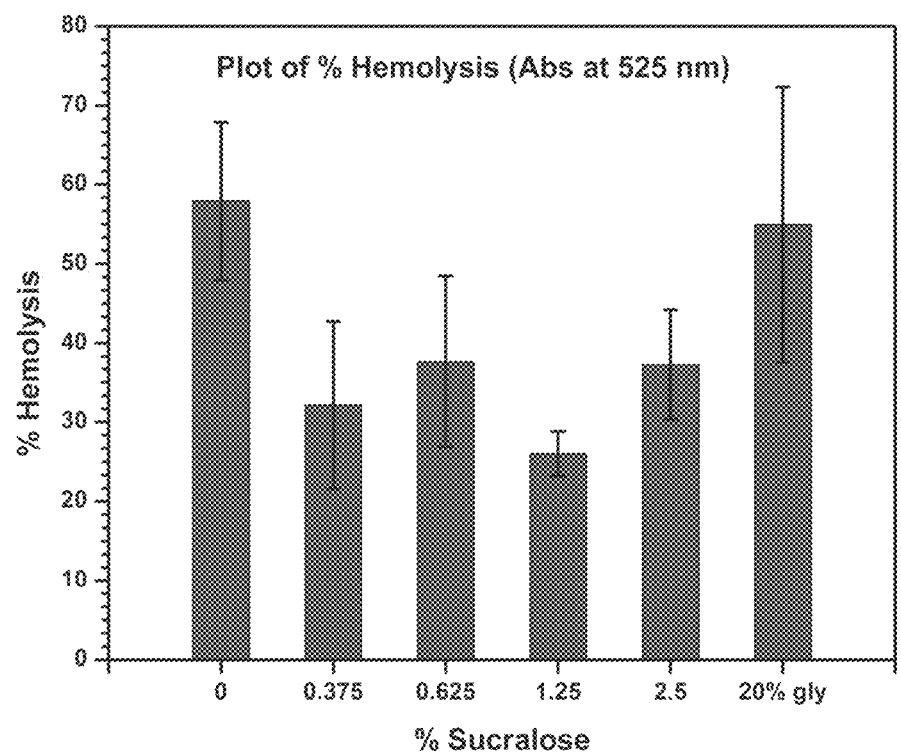

We measured absorption at three wavelengths (450 nm, 500 nm and 525 nm, shown in FIGS. 10, 11 and 12, respectively). Absorption at the wavelength of 450 nm exhibits the highest slope and therefore the greatest sensitivity in determining the percentage of hemolysis of red blood cells. That is why the error bars are smallest for those.

Regardless, it can be seen that the sugar has a protective effect (error bars this time) and it performs better than a 20% v/v solution of glycerol, which is a very important marker. Although we added the same amount of 20% glycerol so the final glycerol % in the blood is lower but it is still a good comparison.

Figure 13:
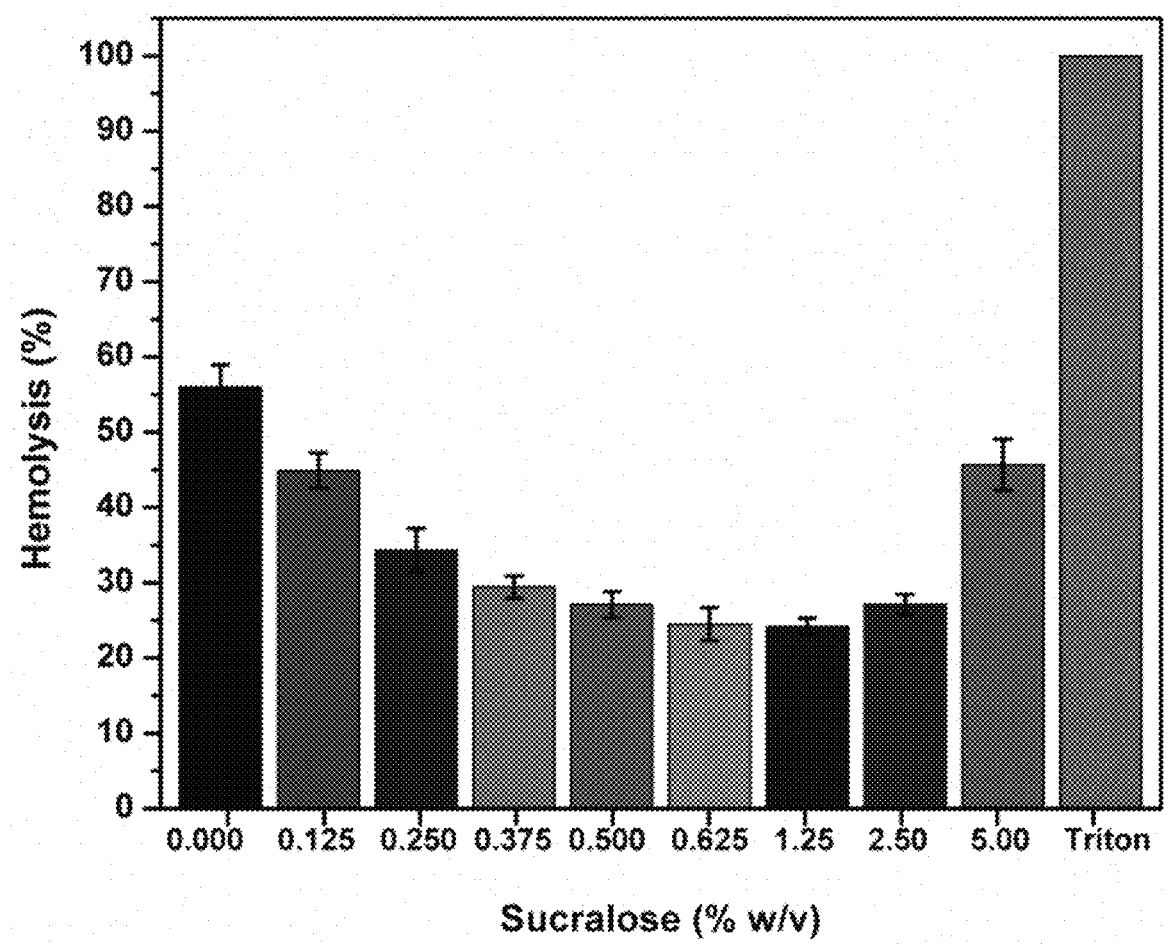
FIG. 13 shows the percent hemolysis of red blood cells frozen with sucralose for 24 hours, and then thawed.

The previous data is a better indicator of real performance, because the blood was stored properly prior to delivery, but this data shows our performance next to glycerol and a relatively small standard deviation at 450 nm. Combining the two data sets, it can be noted that based on these experiments: Sucralose does not induce hemolysis when added to sugar, measured against PBS buffer and triton X; Sucralose offers protection during freezing and substantially reduces hemolysis, measured against triton X and PBS; and the sucralose protective effect is better than using an equivalent volume of a 20% glycerol solution. FIG. 13 shows the cryopreservation of red blood cells frozen at $-80°$ C. for 24 hours in the presence of increasing amounts of sucralose, followed by thawing and determining the percent hemolysis of the red blood cells.

Figure 14A:
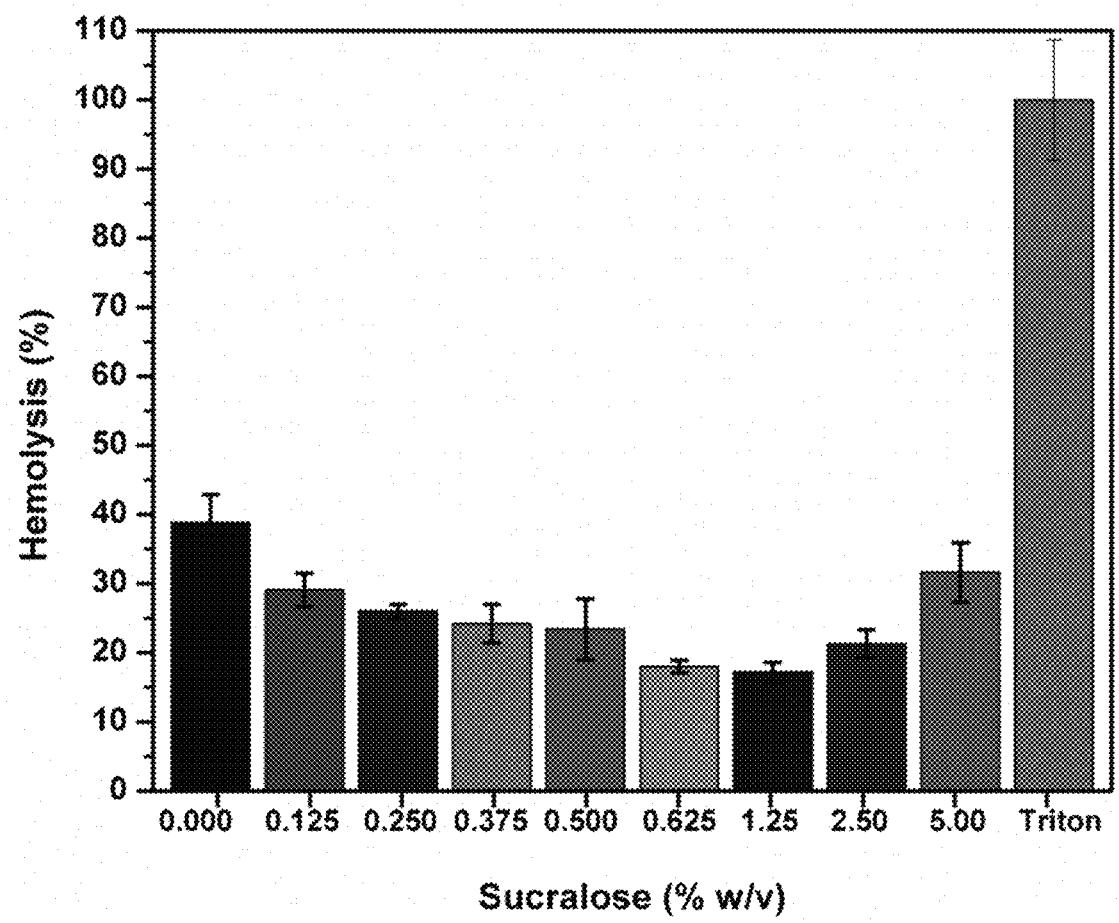
FIG. 14A shows the percent hemolysis of frozen and thawed red blood cells at an original cell count of about 0.2 billion cells/ml in the presence of increasing amounts of sucralose.
Figure 14B:
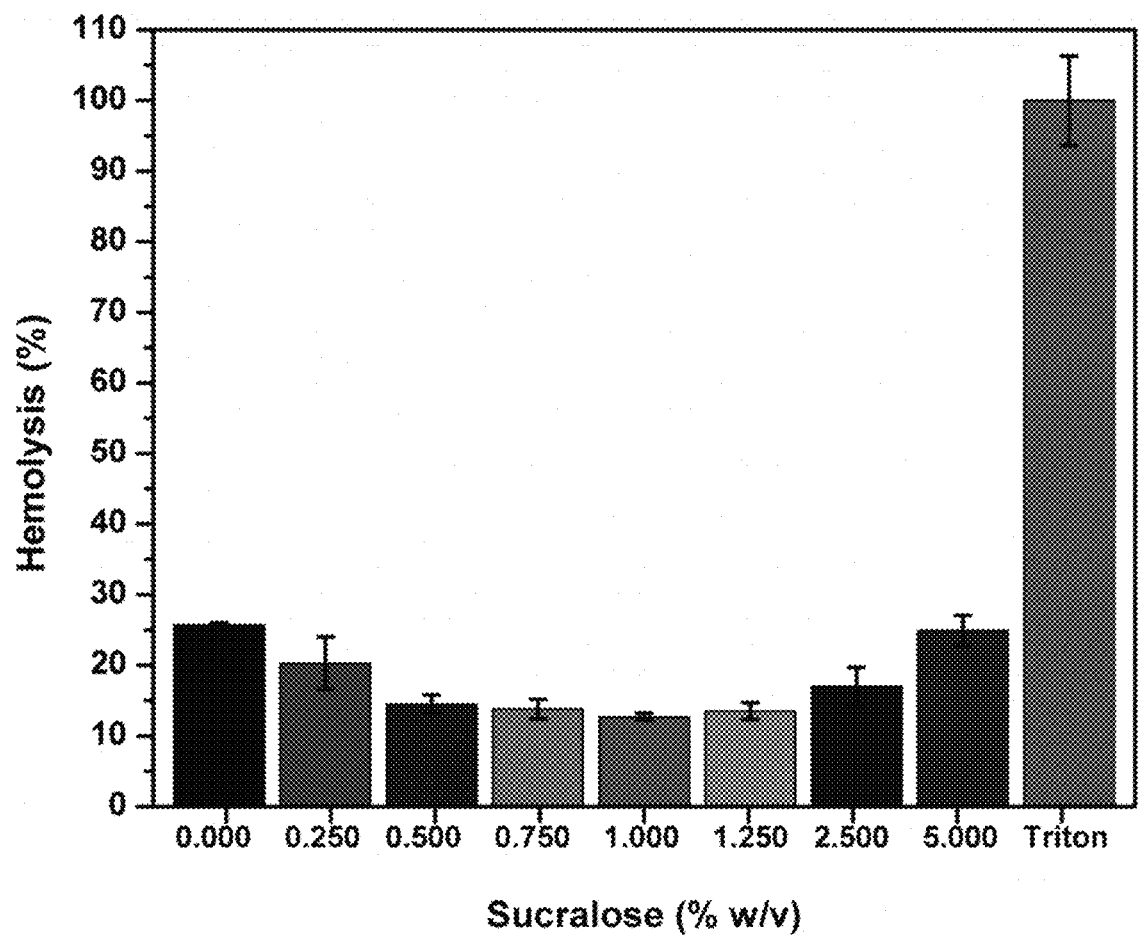
FIG. 14B shows the percent hemolysis of frozen and thawed red blood cells at a cell count of about 0.4 billion cells/ml in the presence of increasing amounts of sucralose.

The amount of sucralose required for cryopreservation of red blood cells increases with an increase of red blood cell concentration. The effect of doubling of red blood cell count on percent hemolysis in the presence of increasing amounts of sucralose is shown in FIGS. 14A and 14B. FIG. 14B shows percentage hemolysis of frozen and thawed red blood cells in the presence of increasing amounts of sucralose at twice the red blood cell concentration (about 0.4 billion cells/ml), then as shown in FIG. 14A (about 0.2 billion cells/ml) These data indicate that as red blood cell concentration is increased, the sugar required to protect the red blood cells from hemolysis increases, but not at the same rate.

Figure 15A:
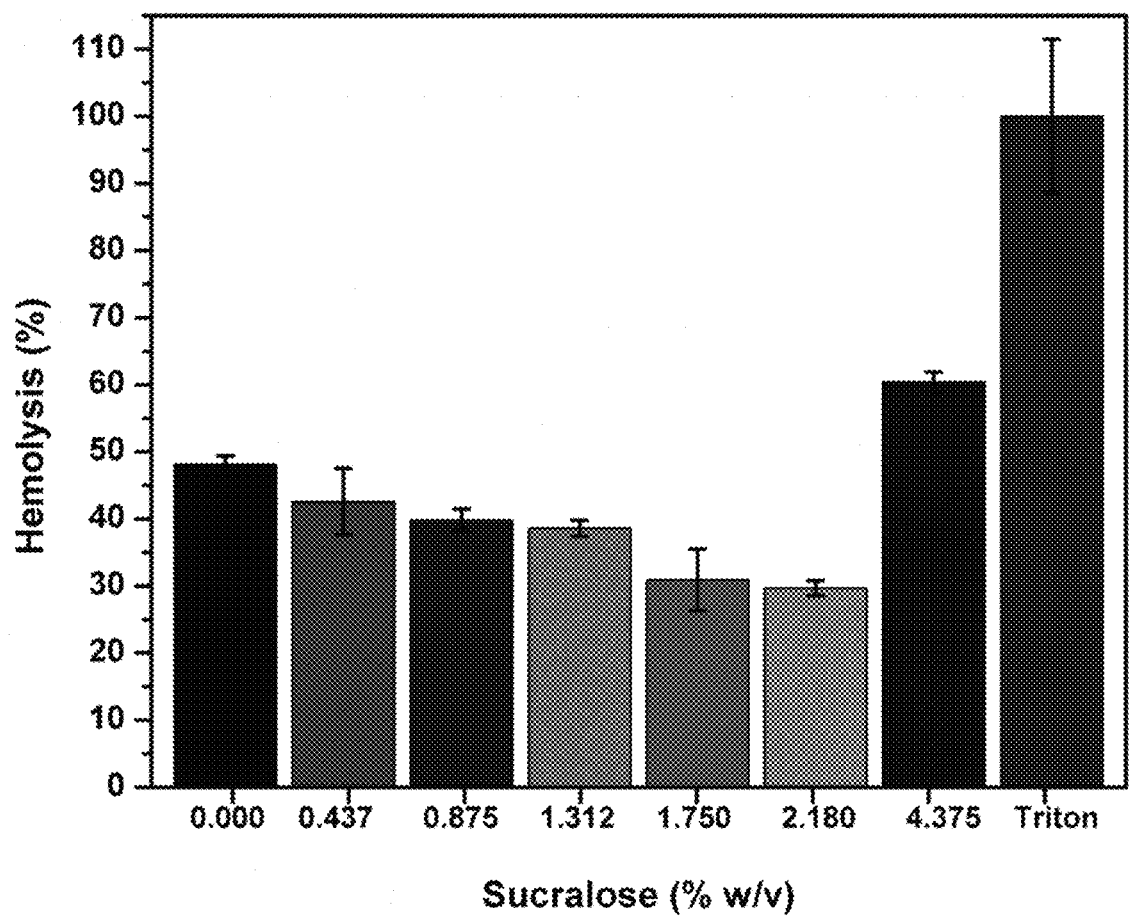
FIG. 15A shows the percent hemolysis of frozen and thawed red blood cells at a cell count of about 0.7 billion cell/ml in the presence of increasing amounts of sucralose.
Figure 15B:
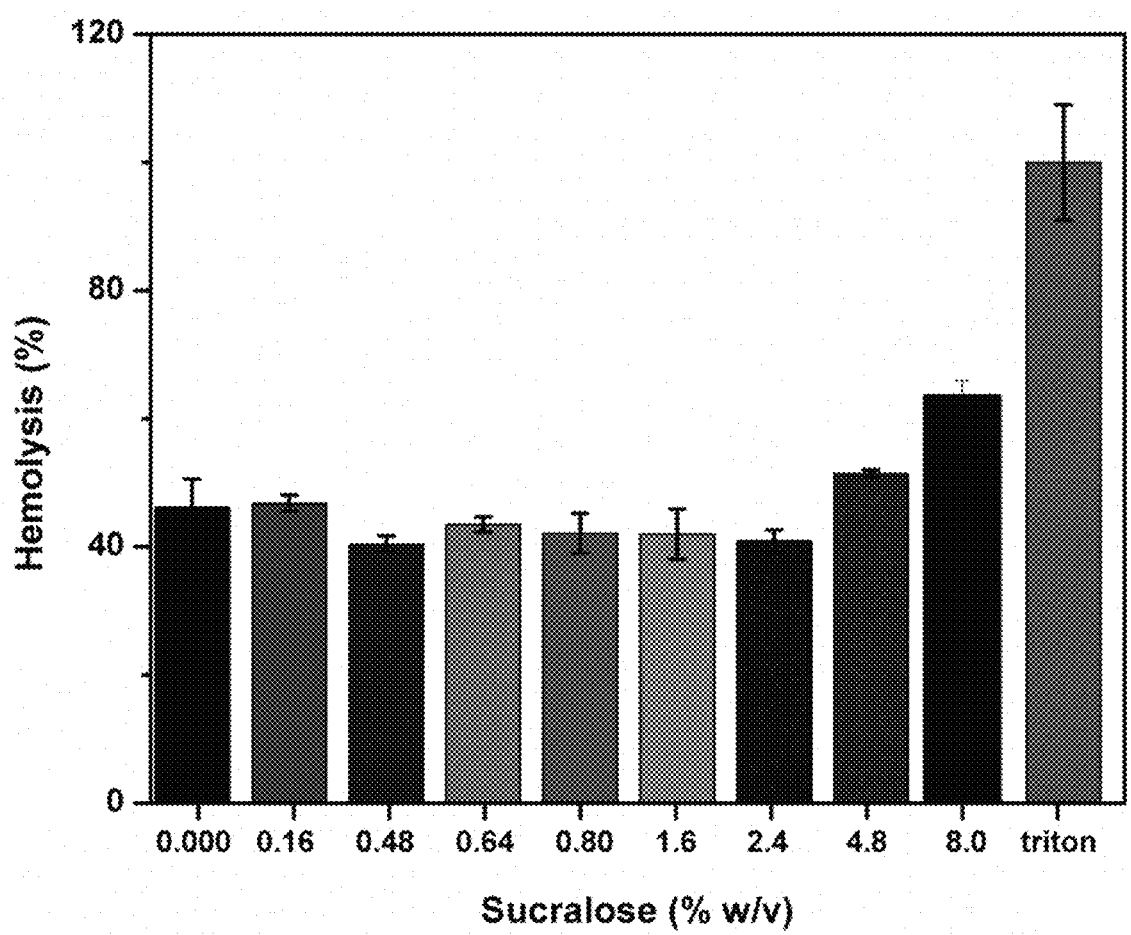
FIG. 15B shows the percent hemolysis of frozen and thawed red blood cells at a cell count of about 1.4 billion cell/ml in the presence of increasing amounts of sucralose.
Figure 13:
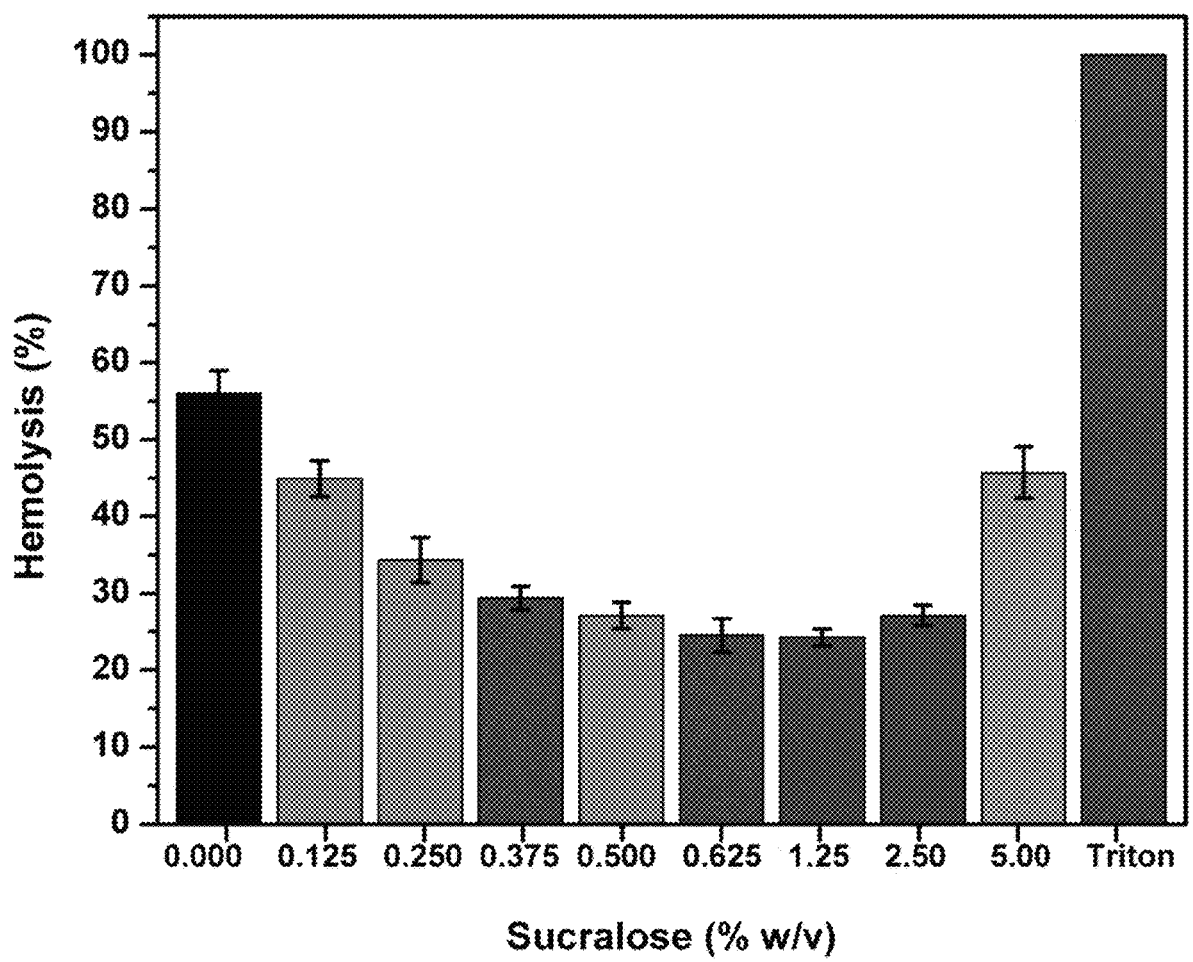
Figure 14A:
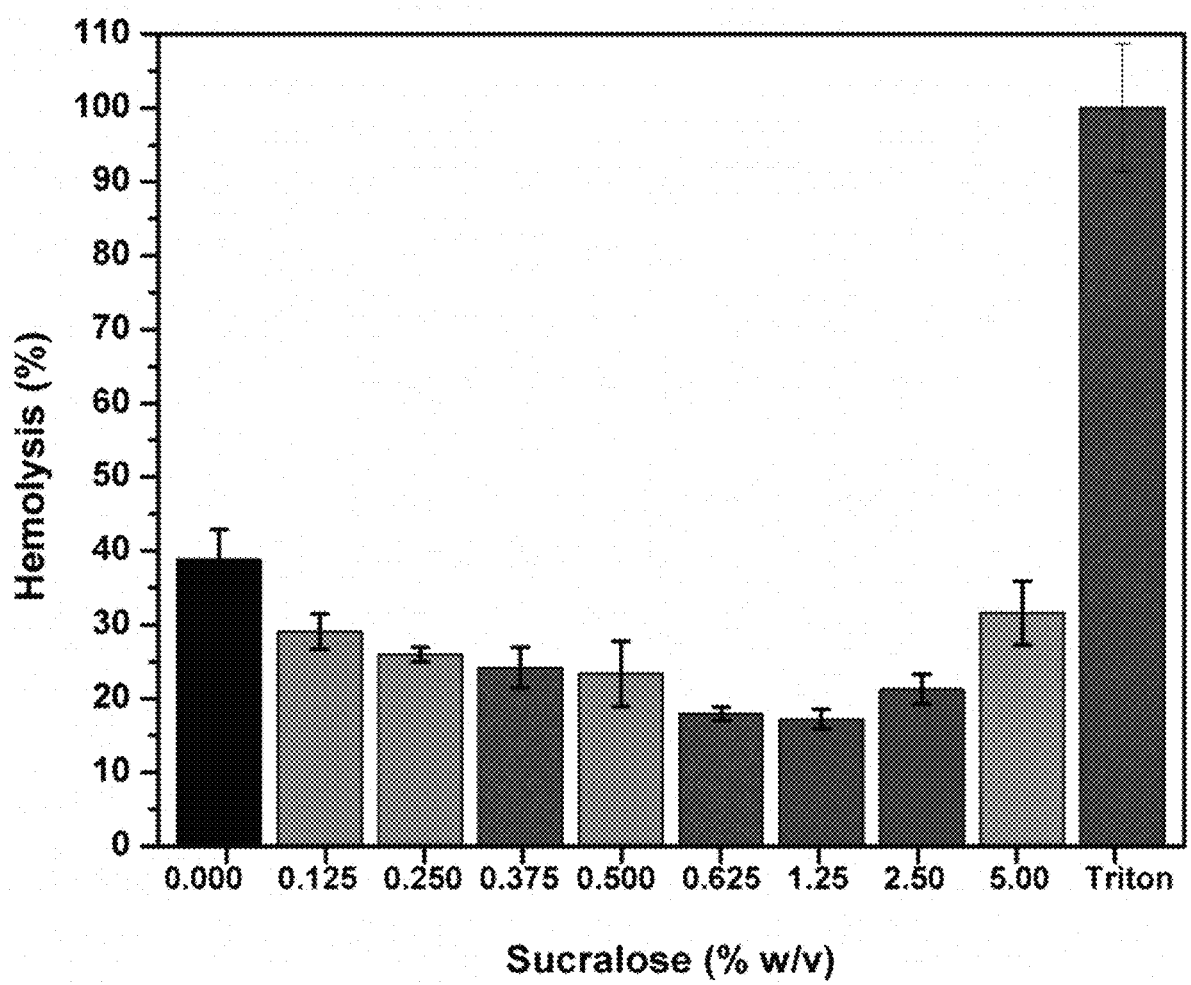
Figure 14B:
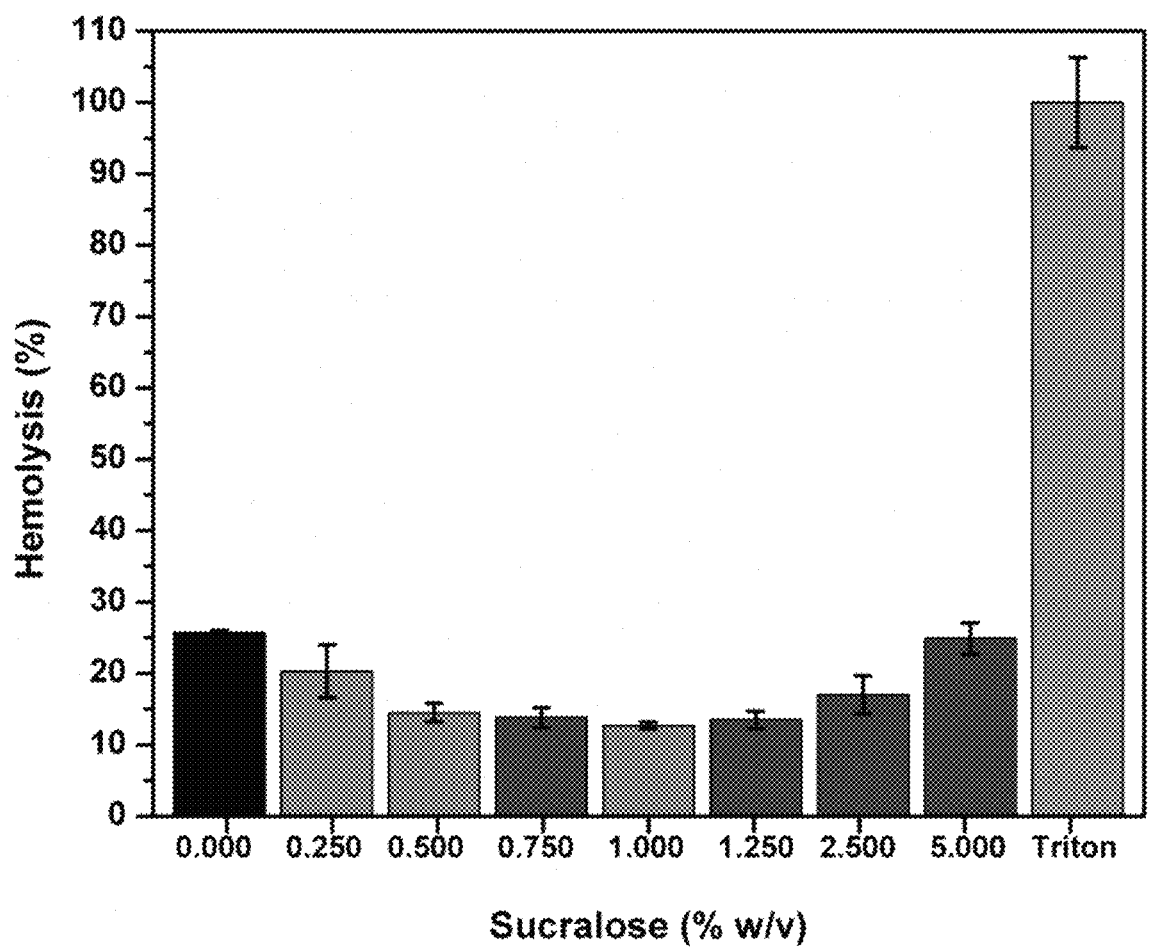
Figure 15A:
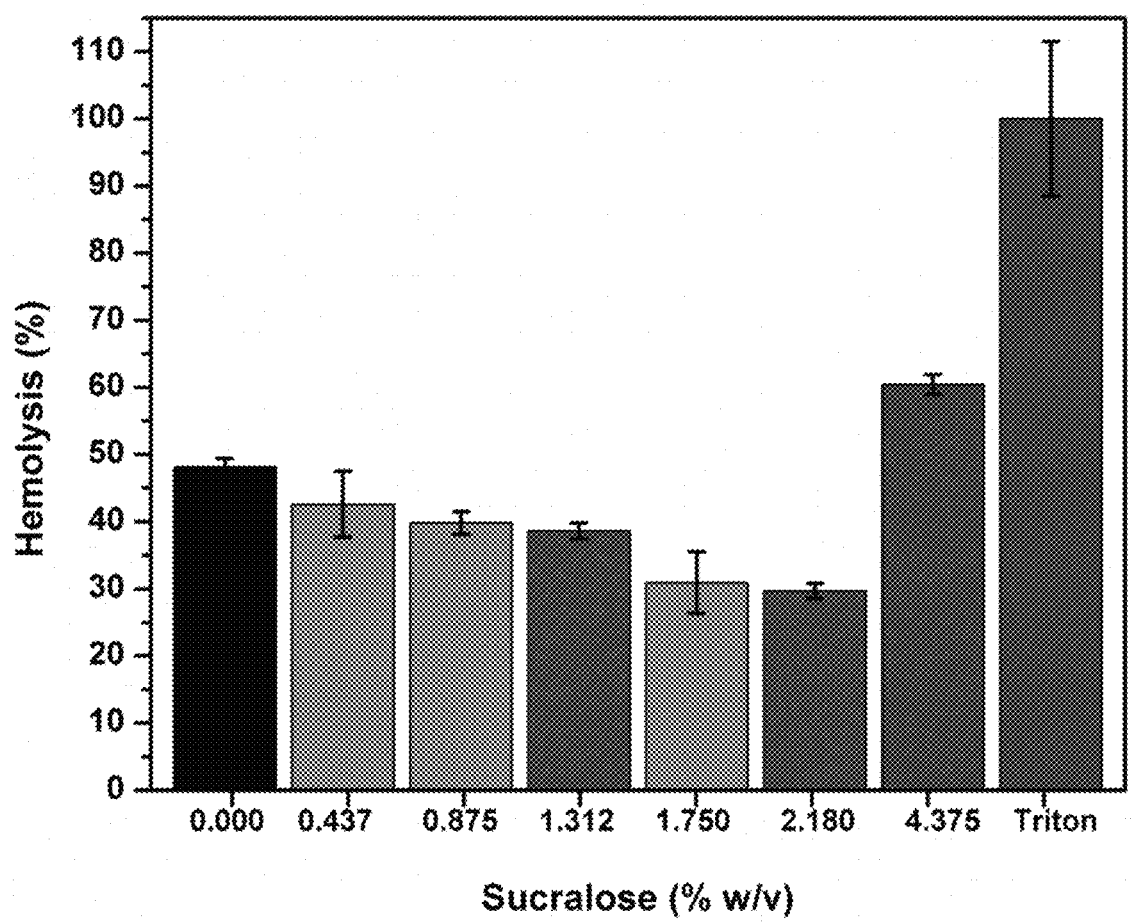
Figure 15B:
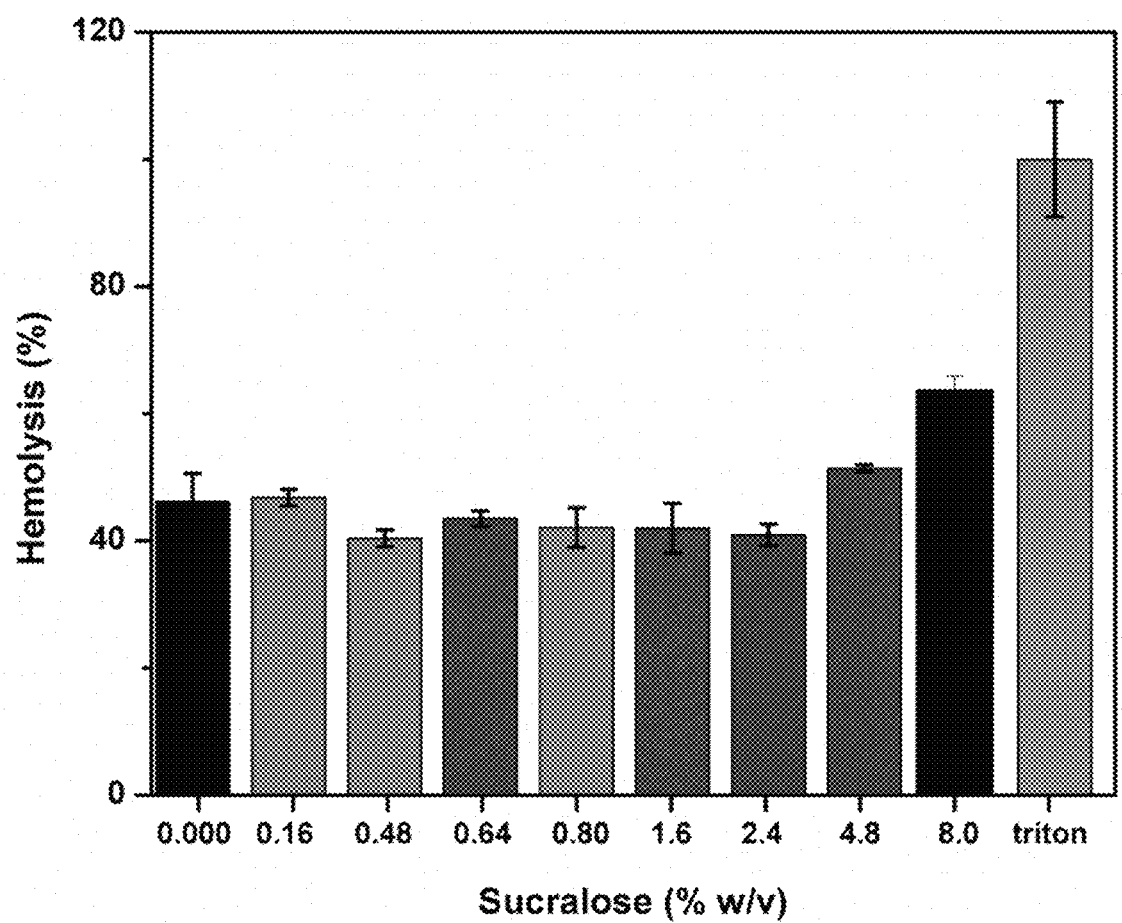

Protection against hemolysis of red blood cells in the presence of increasing amounts of sucralose was examined at 3.5×(~0.7 billion cells/ml) and 7×(~1.4 billion cells/ml) the original red blood cell count, and are shown in FIGS. 15A and 15B, respectively. In addition to indicating that an increased amount of sugar is necessary to protect red blood cells against hemolysis, lower amounts of sugar/sucralose can provide better cryoprotection, and that there is a limit to sugar/sucralose concentration in providing optimum red blood cell cryoprotection. These results indicate that concentrations of sucralose above about 2.5% w/v result in a decreased efficacy in protecting red blood cells from hemolysis. In addition, studies on the cytotoxicity of sucralose on nucleated cells, mouse myoblasts, indicate that sucralose concentrations in excess of about 2.5% w/v may have toxic effects.

These findings provide evidence that sucralose interacts more strongly with the fatty acid chains of a lipid bilayer than sucrose and this is due to differing hydrophobicity. Both sucrose and sucralose may induce phase separation in DPPC bilayers and can further provide a benefit over conventional cyropreservatives.

Example 3

Cryopreservation of Nucleated Cells

Cryopreservation of nucleated cells treated with sucralose is examined. Varying concentrations of sucralose (0% to 25% w/v) is added to representative cell lines. After mixing, sample vials are gradually frozen in liquid nitrogen. Vials are removed at 24 hours, 1 week, 2 weeks and 1 month. After thawing, cells are grown under standard conditions for 24 hours and cell viability is measured using a standard calcein assay. 5% Glycerol (v/v) and 10% (v/v) DMSO and a commercial freezing medium are used as controls.

Example 4

Sucralose as a Lyopreservative

The use of sucralose as a lyopreservative for liposome drug delivery vehicles is examined using a calcein fluorescence leakage assay to quantify membrane damage in model liposome systems following lyophilization. Calcein loaded liposomes is treated with varying concentrations of sucralose (0% to 25% w/v), lyophilized and rehydrated to measure the percentage of leakage. The performance of sucralose is compared to the proven lyopreservative trehalose to ensure sucralose performs at least as well as current technologies.

Example 5

Cryopreservation of Plant Tissue

Cryopreservation of plant tissue is examined by spraying tomato plants with solutions of varying sucralose concentrations (0% to 25% w/v). Seedlings are subjected to overnight freezing by placing them at −10° C. and −20° C. The effectiveness of the solutions is determined measuring the impact of the sugar treatment on fruit production. In a separate study, tomato plants are allowed to produce fruit and are sprayed with a sucralose solution and placed at −10° C. and −20° C. overnight to determine if the sugar solution protects the fruit of the plants.

Example 6

Cryopreservation of Animal Tissue

Preservation of animal tissue is accomplished with whole body perfusion using a sucralose solution. At the time of sacrifice, the heart of an anesthetized mouse is exposed by thoracotomy. 3 mL of sucralose solution (1, 10, 100 mg/g) in PBS is slowly injected into the left ventricle to facilitate perfusion of all internal organs. When the heart has stopped beating, live, lung, pancreas, kidney (others) tissues are removed, immersed in respective sucralose solution, and cryopreserved. After storage at low temperature the organs and tissue are thawed and examined for damage.

The foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A cryopreserved preparation of cells, tissues, organs or plants produced by a process comprising:
   (a) contacting the cell, tissue, organ or plant with a composition comprising from about 0.1% to 2.5% w/v sucralose; and
   (b) freezing the cell, tissue, organ or plant.

2. The cryopreserved preparation of claim 1, wherein the cryopreserved preparation is a transfusable preparation.

3. The cryopreserved preparation of claim 1, wherein the cryopreserved preparation is a transplantable preparation.

4. The cryopreserved preparation of claim 1, wherein the cell is a red blood cell.

5. The cryopreserved preparation of claim 1, wherein the plant is a tomato plant.

6. A kit comprising the cryopreserved preparation of claim 1 and optional instructions for the use thereof.

7. A pharmaceutical composition comprising a cell subjected to a process comprising:
   (a) contacting the cell with a composition comprising from about 0.1% to 2.5% w/v sucralose; and
   (b) freezing the cell.

8. A transplantable preparation comprising a tissue or organ subjected to subjected to a process comprising:
   (a) contacting the tissue or organ with a composition comprising from about 0.1% to 2.5% w/v sucralose; and
   (b) freezing the tissue or organ.

* * * * *